(12) United States Patent
Wright et al.

(10) Patent No.: US 8,836,519 B2
(45) Date of Patent: Sep. 16, 2014

(54) DETERMINING THE ABSENCE OR PRESENCE OF FLUID IN A DIALYSIS SYSTEM

(75) Inventors: Nigel Wright, California, PA (US); Samuel Ernest Magargi, III, Pittsburgh, PA (US); Jeremy Thomas Harbaugh, Cranberry Township, PA (US); Michael John Zang, Allison Park, PA (US); Regis Joseph Winniewicz, Jr., Ellwood City, PA (US); Joseph Stephen Beri, Gibsonia, PA (US); Douglas Mark Zatezalo, Allison Park, PA (US); Tom Monahan, Cranberry Township, PA (US); Ronald Robert Fox, Glenshaw, PA (US)

(73) Assignee: Fresenius Medical Care Holdings, Inc., Waltham, MA (US)

( * ) Notice: Subject to any disclaimer, the term of this patent is extended or adjusted under 35 U.S.C. 154(b) by 236 days.

(21) Appl. No.: 13/468,288

(22) Filed: May 10, 2012

(65) Prior Publication Data
US 2012/0285870 A1   Nov. 15, 2012

Related U.S. Application Data

(63) Continuation-in-part of application No. 13/106,431, filed on May 12, 2011.

(51) Int. Cl.
*G08B 21/00* (2006.01)
*A61M 1/34* (2006.01)

(52) U.S. Cl.
CPC .......... *A61M 1/342* (2013.01); *A61M 2205/14* (2013.01); *A61M 2205/3375* (2013.01); *A61M 2205/12* (2013.01)

USPC ............................................ 340/603; 604/65

(58) Field of Classification Search
CPC .................................. A61M 1/14; G01N 29/02
USPC .............. 340/603, 608; 604/65, 67; 210/645, 210/646; 128/DIG. 13
See application file for complete search history.

(56) References Cited

U.S. PATENT DOCUMENTS 3,871,913 A   3/1975   Shaldon
3,921,622 A   11/1975   Cole (Continued)

FOREIGN PATENT DOCUMENTS

CN   1173635   2/1998
CN   1216275   1/2004

(Continued)

OTHER PUBLICATIONS

"RX Guide to Custom Dialysis," COBE Renal Care Inc., Revision E. Sep. 1993.

(Continued)

*Primary Examiner* — Jeffery Hofsass
(74) *Attorney, Agent, or Firm* — Fish & Richardson P.C.

(57) ABSTRACT

This disclosure relates to detecting fluid in medical tubing. In certain aspects, a method is performed by a data processing apparatus. The method includes controlling repetitive activation of the ultrasonic transmitter. The method also includes receiving a signal from the ultrasonic receiver during an activation of the ultrasonic transmitter. The method also includes determining that fluid is absent or present in a portion of the medical fluid tube based on a comparison between the signal and a threshold value.

22 Claims, 10 Drawing Sheets

(56) References Cited

U.S. PATENT DOCUMENTS

| | | | |
|---|---|---|---|
| 3,935,876 A * | 2/1976 | Massie et al. ............... 137/177 |
| 4,068,521 A | 1/1978 | Cosentino et al. |
| 4,174,231 A | 11/1979 | Hobgood |
| 4,191,351 A | 3/1980 | Goyne |
| 4,341,116 A | 7/1982 | Bilstad et al. |
| 4,581,141 A | 4/1986 | Ash |
| 4,666,598 A | 5/1987 | Heath et al. |
| 4,673,927 A * | 6/1987 | Cianciavicchia et al. ..... 340/621 |
| 4,684,460 A | 8/1987 | Issautier |
| 4,728,496 A | 3/1988 | Petersen et al. |
| 4,730,493 A | 3/1988 | Lebaud et al. |
| 4,770,787 A | 9/1988 | Heath et al. |
| 4,784,495 A | 11/1988 | Jonsson et al. |
| 4,789,467 A | 12/1988 | Lindsay et al. |
| 4,797,655 A | 1/1989 | Orndal et al. |
| 4,909,786 A | 3/1990 | Gijselhart et al. |
| 4,966,579 A | 10/1990 | Polaschegg |
| 4,981,467 A | 1/1991 | Bobo, Jr. et al. |
| 4,997,577 A | 3/1991 | Stewart |
| 5,064,412 A | 11/1991 | Henke et al. |
| 5,102,392 A | 4/1992 | Sakai et al. |
| 5,176,631 A | 1/1993 | Koenig |
| 5,179,862 A | 1/1993 | Lynnworth |
| 5,211,201 A | 5/1993 | Kamen et al. |
| 5,256,371 A | 10/1993 | Pippert |
| 5,262,068 A | 11/1993 | Bowers et al. |
| 5,277,820 A | 1/1994 | Ash |
| 5,304,349 A | 4/1994 | Polaschegg |
| 5,392,638 A | 2/1995 | Kawahara |
| 5,394,732 A | 3/1995 | Johnson et al. |
| 5,409,612 A | 4/1995 | Maltais et al. |
| 5,421,813 A | 6/1995 | Ohnishi |
| 5,453,576 A | 9/1995 | Krivitski |
| 5,496,273 A | 3/1996 | Pastrone et al. |
| 5,536,412 A | 7/1996 | Ash |
| 5,589,070 A | 12/1996 | Maltais et al. |
| 5,591,344 A | 1/1997 | Kenley et al. |
| 5,603,902 A | 2/1997 | Maltais et al. |
| 5,605,630 A | 2/1997 | Shibata |
| 5,641,892 A | 6/1997 | Larkins et al. |
| 5,685,989 A | 11/1997 | Krivitski et al. |
| 5,713,125 A | 2/1998 | Watanabe et al. |
| 5,755,563 A | 5/1998 | Clegg et al. |
| 5,788,099 A | 8/1998 | Treu et al. |
| 5,830,365 A | 11/1998 | Schneditz |
| 5,919,369 A | 7/1999 | Ash |
| 5,935,099 A | 8/1999 | Peterson et al. |
| 5,944,684 A | 8/1999 | Roberts et al. |
| 6,000,567 A | 12/1999 | Carlsson et al. |
| 6,036,858 A | 3/2000 | Carlsson et al. |
| 6,044,691 A | 4/2000 | Kenley et al. |
| 6,085,574 A | 7/2000 | Neftel et al. |
| 6,086,753 A | 7/2000 | Ericson et al. |
| 6,142,008 A | 11/2000 | Cole et al. |
| 6,143,181 A | 11/2000 | Falkvall et al. |
| 6,170,785 B1 | 1/2001 | Lampropoulos |
| 6,190,855 B1 | 2/2001 | Herman et al. |
| 6,277,277 B1 | 8/2001 | Jacobi et al. |
| 6,280,632 B1 | 8/2001 | Polaschegg |
| 6,308,721 B1 | 10/2001 | Bock et al. |
| 6,409,699 B1 | 6/2002 | Ash |
| 6,416,293 B1 | 7/2002 | Bouchard et al. |
| 6,428,706 B1 | 8/2002 | Rosenqvist et al. |
| 6,515,487 B1 | 2/2003 | Dawson et al. |
| 6,542,761 B1 | 4/2003 | Jahn et al. |
| 6,622,542 B2 | 9/2003 | Derek et al. |
| 6,731,971 B2 | 5/2004 | Evans, III et al. |
| 6,755,976 B2 | 6/2004 | Rosenqvist et al. |
| 6,796,195 B2 | 9/2004 | Povey et al. |
| 6,806,947 B1 | 10/2004 | Ekdahl et al. |
| 6,821,432 B2 | 11/2004 | Metzner |
| 6,878,283 B2 | 4/2005 | Thompson |
| 7,033,498 B2 | 4/2006 | Wong |
| 7,047,809 B2 | 5/2006 | Cobb |
| 7,077,956 B2 | 7/2006 | Rovatti |
| 7,241,272 B2 | 7/2007 | Karoor et al. |
| 7,243,541 B1 | 7/2007 | Bey et al. |
| 7,481,114 B2 | 1/2009 | Lynnworth |
| 7,661,293 B2 | 2/2010 | Dam |
| 7,661,294 B2 | 2/2010 | Dam |
| 7,947,179 B2 | 5/2011 | Rosenbaum et al. |
| 2002/0079695 A1 | 6/2002 | Campbell et al. |
| 2002/0104370 A1 | 8/2002 | Steger et al. |
| 2003/0105424 A1 | 6/2003 | Karoor et al. |
| 2004/0019312 A1 | 1/2004 | Childers |
| 2004/0050789 A1 | 3/2004 | Ash |
| 2005/0274658 A1 | 12/2005 | Rosenbaum et al. |
| 2006/0052963 A1 | 3/2006 | Shkarlet |
| 2006/0277977 A1 | 12/2006 | Kahn et al. |
| 2007/0093160 A1 | 4/2007 | Collins |
| 2007/0158247 A1 | 7/2007 | Carr et al. |
| 2007/0158249 A1 | 7/2007 | Ash |
| 2007/0158268 A1 | 7/2007 | DeComo |
| 2007/0161113 A1 | 7/2007 | Ash |
| 2007/0161941 A1 | 7/2007 | Ash et al. |
| 2007/0181499 A1 | 8/2007 | Roberts et al. |
| 2008/0098798 A1 | 5/2008 | Riley et al. |
| 2008/0149563 A1 | 6/2008 | Ash |
| 2008/0177216 A1 | 7/2008 | Ash |
| 2009/0012455 A1 | 1/2009 | Childers et al. |
| 2009/0078047 A1 | 3/2009 | Dam |
| 2009/0088687 A1 | 4/2009 | Yardimci et al. |
| 2009/0114595 A1 | 5/2009 | Wallenas et al. |

FOREIGN PATENT DOCUMENTS

| | | |
|---|---|---|
| CN | 1969185 | 5/2007 |
| CN | 1578903 | 4/2008 |
| EP | 0238809 A2 | 9/1987 |
| EP | 0 278 100 | 8/1988 |
| EP | 446605 | 9/1991 |
| EP | 0467805 A1 | 1/1992 |
| EP | 0 673 658 | 9/1995 |
| EP | 0813041 | 12/1997 |
| EP | 1 342 480 | 9/2003 |
| JP | 04158258 | 6/1992 |
| JP | 09178712 | 7/1997 |
| JP | 2002-333434 | 11/2002 |
| JP | 2003-043017 | 2/2003 |
| KR | 10-0157986 | 11/1998 |
| KR | 10-2002-0063001 | 7/2002 |
| KR | 10-2003-0035584 | 5/2003 |
| KR | 10-0516727 | 9/2005 |
| WO | WO 96/40322 | 12/1996 |
| WO | WO 98/17333 | 4/1998 |
| WO | WO 99/37342 | 7/1999 |
| WO | WO 01/92867 | 12/2001 |
| WO | WO 02/30267 | 4/2002 |
| WO | WO 02/43859 | 6/2002 |
| WO | WO 03/040702 | 5/2003 |
| WO | WO 2005/111602 | 11/2005 |
| WO | WO 2005/123230 | 12/2005 |
| WO | WO 2007/028056 | 3/2007 |
| WO | WO 2007/081383 | 7/2007 |
| WO | WO 2007/081384 | 7/2007 |
| WO | WO 2007/081565 | 7/2007 |
| WO | WO 2007/081576 | 7/2007 |
| WO | WO 2009/042061 | 4/2009 |

OTHER PUBLICATIONS

"Sorbent Dialysis Pimer," COBE Renal Care, Inc., Sep. 4, 1993 Ed.
Blumenkrantz et al., "Artif Organs," 3(3):230-236, 1978.
Operator's Manual—Fresenius 2008K Hemodialysis Machine (2000).
International Search Report and Written Opinion from corresponding PCT Application No. PCT/US2012/037225, mailed Aug. 20, 2012, 14 pages.

* cited by examiner

DETERMINING THE ABSENCE OR PRESENCE OF FLUID IN A DIALYSIS SYSTEM

CROSS-REFERENCE TO RELATED APPLICATIONS

This application is a continuation in part of, and claims priority to, U.S. patent application Ser. No. 13/106,431, filed on May 12, 2011, entitled "Medical Tubing Installation Detection," the entire contents of which are hereby incorporated by reference.

TECHNICAL FIELD

This invention relates to medical tubing installation detection.

BACKGROUND

When kidney failure is diagnosed, patients are typically given medication to help control the symptoms and slow the progress of damage to the kidneys. Patients with chronic kidney failure generally take drugs to control the balance of minerals in the body and prevent a reduction of red blood cells (anemia).

Healthy kidneys produce the hormone erythropoietin (often shortened to "EPO"), which stimulates the production of red blood cells in bone marrow. Red blood cells play a key role in the delivery of oxygen to tissues in the body. Insufficient levels of EPO in the body can lead to anemia. This often causes a drop in physical and mental performance and an increased risk for cardio-vascular diseases. To prevent anemia, chronic renal patients frequently receive a synthetic version of erythropoietin (also referred to as "EPO") that, like the natural erythropoietin, stimulates the production of red blood cells.

Anemia can be managed using a variety of different drugs. For example, since iron is also needed to produce red blood cells, many dialysis patients also take iron preparations. Venofer® (iron sucrose injection, USP) is indicated in the treatment of iron deficiency anemia in patients undergoing chronic hemodialysis who are receiving supplemental EPO therapy.

SUMMARY

In one aspect of the invention, a method is performed by a data processing apparatus. The method includes detecting that a tube is incorrectly installed on a drug delivery device by providing an instruction for a motor of the drug delivery device to pump a drug and receiving, after a period of time has passed since providing the instruction for the motor of the drug delivery device to pump the drug, a signal from a fluid detector connected to the tube, the signal indicating an absence of fluid in the tube.

In another aspect of the invention, a second method is performed by a data processing apparatus. The method includes detecting that a tube is incorrectly installed on a drug delivery device by receiving a first signal from a fluid detector connected to the tube, determining a first magnitude of the first signal from the fluid detector, and storing the first magnitude of the first signal. The method also includes receiving, at a later time, a second signal from the fluid detector connected to the tube and determining a second magnitude of the second signal from the fluid detector. The method also includes comparing the first and second magnitudes and determining that the second magnitude is a threshold level greater than the first magnitude.

In another aspect of the invention, a dialysis system includes a dialysis machine, a control unit, a medical fluid tube connected to the dialysis machine, and a fluid detector. The dialysis system also includes a computer-readable medium coupled to the control unit having instructions stored thereon which, when executed by the one or more processors, cause the one or more processors to perform operations. The operations include detecting that a tube is incorrectly installed on a drug delivery device by providing an instruction for a motor of the drug delivery device to pump a drug and receiving, after a period of time has passed since providing the instruction for the motor of the drug delivery device to pump the drug, a signal from a fluid detector connected to the tube, the signal indicating an absence of fluid in the tube.

In another aspect of the invention, a dialysis system includes a dialysis machine, a control unit, a medical fluid tube connected to the dialysis machine, and a fluid detector. The dialysis system also includes a computer-readable medium coupled to the control unit having instructions stored thereon which, when executed by the one or more processors, cause the one or more processors to perform operations. The operations include detecting that a tube is incorrectly installed on a drug delivery device by receiving a first signal from a fluid detector connected to the tube, determining a first magnitude of the first signal from the fluid detector, and storing the first magnitude of the first signal. The method also includes receiving, at a later time, a second signal from the fluid detector connected to the tube and determining a second magnitude of the second signal from the fluid detector. The method also includes comparing the first and second magnitudes and determining that the second magnitude is a threshold level greater than the first magnitude.

In another aspect of the invention, a dialysis system includes a dialysis machine, a control unit, a medical fluid tube connected to the dialysis machine, an ultrasonic transmitter positioned adjacent to the medical fluid tube, and an ultrasonic receiver positioned adjacent to the medical fluid tube configured to receive one or more signals in response to the activation of the ultrasonic transmitter. The dialysis system also includes a computer storage medium encoded with computer program instructions that when executed by dialysis system, causes the dialysis system to perform operations comprising controlling repetitive activation of the ultrasonic transmitter. The operations also include receiving a signal from the ultrasonic receiver during an activation of the ultrasonic transmitter. The operations also include determining that fluid is absent or present in a portion of the medical fluid tube based on a comparison between the signal and a threshold value.

Implementations can include one or more of the following features.

In certain implementations, the tube has an external diameter less than 0.01 inch.

In certain implementations, the fluid detector is connected to the tube upstream of the pump.

In certain implementations, the fluid detector is connected between a drug vial and the pump.

In certain implementations, the fluid detector is an ultrasonic fluid detector.

In some implementations, the drug delivery device includes only one ultrasonic fluid detector connected to the tube.

In certain implementations, the method includes receiving, prior to providing the instruction for the motor of the drug delivery device to pump the drug, a signal from the fluid detector, the signal indicating an absence of fluid in the tube.

In certain implementations, providing the instruction for the motor to pump the drug includes providing the instruction for a duration such that the drug is drawn from a drug vial to fill the tube up to the pump.

In some implementations, the signal is received after the duration for which the instruction is provided.

In certain implementations, the drug delivery device is a module that fits into a dialysis machine.

In certain implementations, the method includes providing a visual indication that the tube is incorrectly installed.

In some implementations, the method includes providing an instruction for a motor of the drug delivery device to pump a drug prior to receiving the second signal from the fluid detector.

In certain implementations, the first signal is received after a drug has been pumped from the drug vial to fill the tube up to the pump.

In certain implementations, the operations include storing an indicator of the absence or presence of fluid in a data structure, the data structure storing a plurality of indicators determined during previous activations of the ultrasonic transmitter.

In certain implementations, the operations include raising an alert upon determining that each indicator in the data structure indicates that fluid was absent from the portion of the medical fluid tube.

In certain implementations, controlling repetitive activation of the ultrasonic transmitter includes, for each repetition, activating the ultrasonic transmitter for a first period and deactivating the ultrasonic transmitter for a second period.

In certain implementations, the first period is less than 10 milliseconds.

The certain implementations, the medical fluid tube has an outer diameter of less than 0.128 inch.

The certain implementations, the medical fluid tube has an inner diameter of less than 0.031 inch.

In certain implementations, the signal is a measure of voltage.

In certain implementations, the threshold value is a first value if fluid was determined to be present during the previous activation of the ultrasonic transmitter, the threshold is a second value if the fluid was previously determined to be absent during the previous activation of the ultrasonic transmitter, and the first value is greater than the second value.

Implementations can include one or more of the following advantages.

In some implementations, the methods described reduce the number of false positive alerts caused by small air bubbles passing through a medical fluid tube. The methods described reduce cavitation in the medical fluid tube.

DETAILED DESCRIPTION

In general, the invention relates to methods for detecting whether medical fluid tubing is correctly installed on a hemodialysis system and/or controlling repetitive activation of an ultrasonic transmitter to reduce cavitation in fluid within a medical fluid tube. In some aspects of the invention, a hemodialysis system includes a hemodialysis machine having a drug delivery device including one or more pumps and drug delivery lines connected to a blood circuit. In this way, drug can be delivered to the blood circuit. A control unit controls aspects of the hemodialysis system, including executing the methods further described below. The control unit is used to determine correct installation of the medical fluid tubing. In some implementations, the medical fluid tubing is too small in diameter (e.g., less than 0.1 inch or less than 0.3 inch) to be effectively detected by sensors designed to detect the presence of conventional, larger medical tubing. By using a combination of commands provided by the control unit and signals received by the control unit, the control unit can determine whether the tubing has been properly installed. The signals received, for example, can be from a fluid detector or other sensors that do not directly provide information regarding the presence of the tube.

Figure 1:
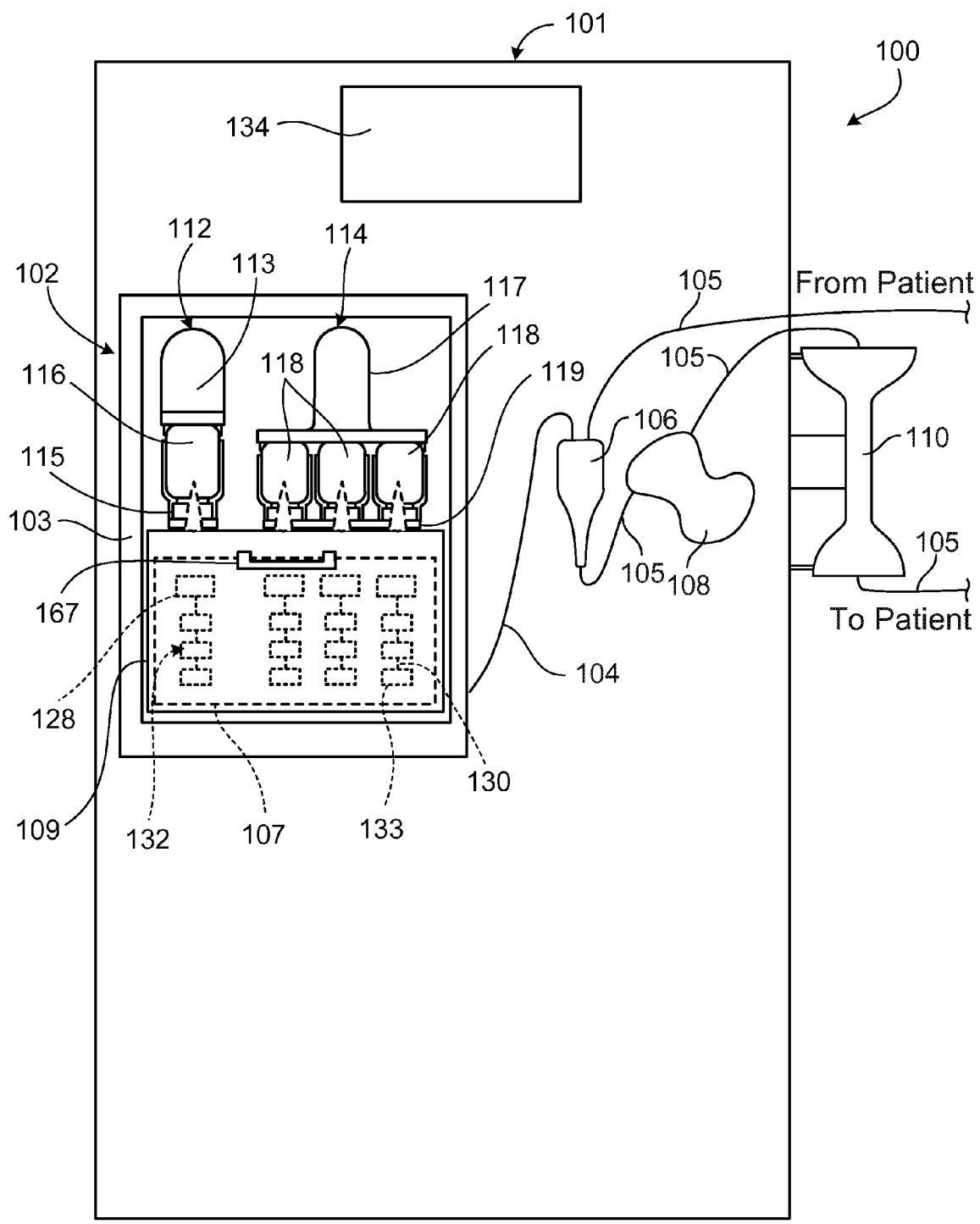
FIG. 1 is a schematic of a hemodialysis machine that includes a modular drug delivery device and a drug administration fluid line cassette secured between a door and inner face of the modular drug delivery device. The hemodialysis machine further includes fluid sensor assemblies that can determine whether fluids have been introduced into a fluid line engaged with the fluid sensor assemblies.

Referring to FIG. 1, a hemodialysis system 100 includes a hemodialysis machine 101 that has a drug delivery system 102. The drug delivery system 102 includes a modular drug delivery device 103 that is attached to and exposed on the face of the hemodialysis machine 101 and a disposable drug administration fluid line set (also referred to herein as a drug administration fluid line cassette) 107 that is connected to the drug delivery device 103. A drug delivery line (tube) 104 of the drug administration fluid line cassette 107 is fluidly connected to a blood circuit of the hemodialysis system 100. The blood circuit of the hemodialysis system 100 includes, among other things, a series of blood lines (tubes) 105, a drip chamber 106, and a dialyzer 110. A blood pump (e.g., a peristaltic pump) 108 is configured to pump blood through the blood circuit during treatment.

The drug delivery device 103 also includes a control unit (e.g., a microprocessor) that can control various components of the drug delivery device 103. As will be described in greater detail below, the control unit can receive signals from and send signals to the various components of the drug delivery device 103. The control unit can control the various components of the drug delivery device 103 based on information received from these components to ensure correct installation of the drug administration fluid line set 107, and to ensure a correct amount of drug is delivered to the patient. In some implementations, for example, the control unit can receive signals from fluid detectors that indicate the presence or absence of fluid in the fluid lines. The control unit can also provide instructions to motors of pumps to draw fluid from drug vials. A combination of these signals and instructions at appropriate times can enable the control unit to determine whether the fluid lines are properly installed.

The hemodialysis system 100 also includes a dialysate circuit and various other components that, for the sake of simplicity, will not be described in detail. During hemodialysis treatment, blood is drawn from the patient and, after passing through the drip chamber 106, is pumped through the dialyzer 110 where toxins are removed from the blood and collected in dialysate passing through the dialyzer. The cleansed blood is then returned to the patient, and the dialysate including the toxins (referred to as "spent dialysate") is disposed of or recycled and reused. During the hemodialysis treatment, drugs (e.g., Epogen® and Venofer®) are also delivered to the drip chamber 106 using the drug delivery system 102. The drugs mix with the patient's blood within the drip chamber 106 and are then delivered to the patient along with the patient's blood.

Still referring to FIG. 1, the modular drug delivery device 103 includes a drug vial holder 112 configured to hold a single drug vial 116. Another drug vial holder 114 is configured to hold up to three drug vials 118. In the illustrated implementation, the vial 116 furthest to the left contains Venofer® and the three vials 118 to the right of the Venofer® vial 116 contain Epogen®. Venofer® (iron sucrose injection, USP) is a sterile, aqueous complex of polynuclear iron (III)-hydroxide in sucrose that is manufactured by American Regent, Inc. Venofer® is indicated in the treatment of iron deficiency anemia in patients undergoing chronic hemodialysis who are receiving supplemental erythropoietin therapy. Epogen® is a drug that stimulates the production of red blood cells and is also commonly used in dialysis patients. Epogen® is manufactured by Amgen, Inc.

The drug vial holder 112 includes a top member 113 and a bottom member 115 that can retain the single Venofer® vial 116 therebetween. The bottom member 115 has a top surface on which the cap of the inverted Venofer® vial 116 can rest. In certain implementations, the bottom member 115 includes a recess that is sized and shaped to receive a cap (or a portion of the cap) of the vial 116. This recess can help to ensure that the vial 116 is properly positioned in the vial holder 112. The bottom member 115 of the drug vial holder 112 also defines a through opening that allows an associated spike 120 of the drug administration fluid line cassette 107 (shown in FIG. 2) to pass through the bottom member 113 and pierce a rubber seal of the Venofer® vial 116 during use.

The top and bottom members 113, 115 of the drug vial holder 112 are moveable relative to one another such that a drug vial can be compressed there between. In addition, the drug vial holder 112 as a whole is moveable in the vertical direction relative to the front face of the drug delivery device 103 and relative to an associated spike 120 of the drug administration fluid line cassette 107 when the cassette 107 is disposed in the cassette compartment of the drug delivery device 103. As a result, when the cassette 107 is disposed in the cassette compartment, the top and bottom members 113, 115 of the drug vial holder 112 can be moved in unison along with the Venofer® vial 116 to cause the associated spike 120 of the cassette 107 to pierce the rubber seal of the vial 116.

The drug vial holder 114, which holds the Epogen® vials 118 during use, is similar to the drug vial holder 112 described above. In particular, this drug vial holder 114 also includes top and bottom members 117, 119 between which three Epogen® vials 118 can be held, and the bottom member 119 defines three openings through which spikes 120 of the cassette 107 can pass to pierce rubber seals of the vials 118. In some implementations, the upper surface of the bottom member 119 defines recesses that receive the caps of the Epogen® vials 118 and help to ensure that the vials 118 are properly positioned in the vial holder 114. These recesses can, for example, help to ensure that the vials 118 are aligned with the openings in the bottom member 119 to allow the spikes 120 of the cassette 107 to pierce the rubber seals of the vials 118.

Figure 2:
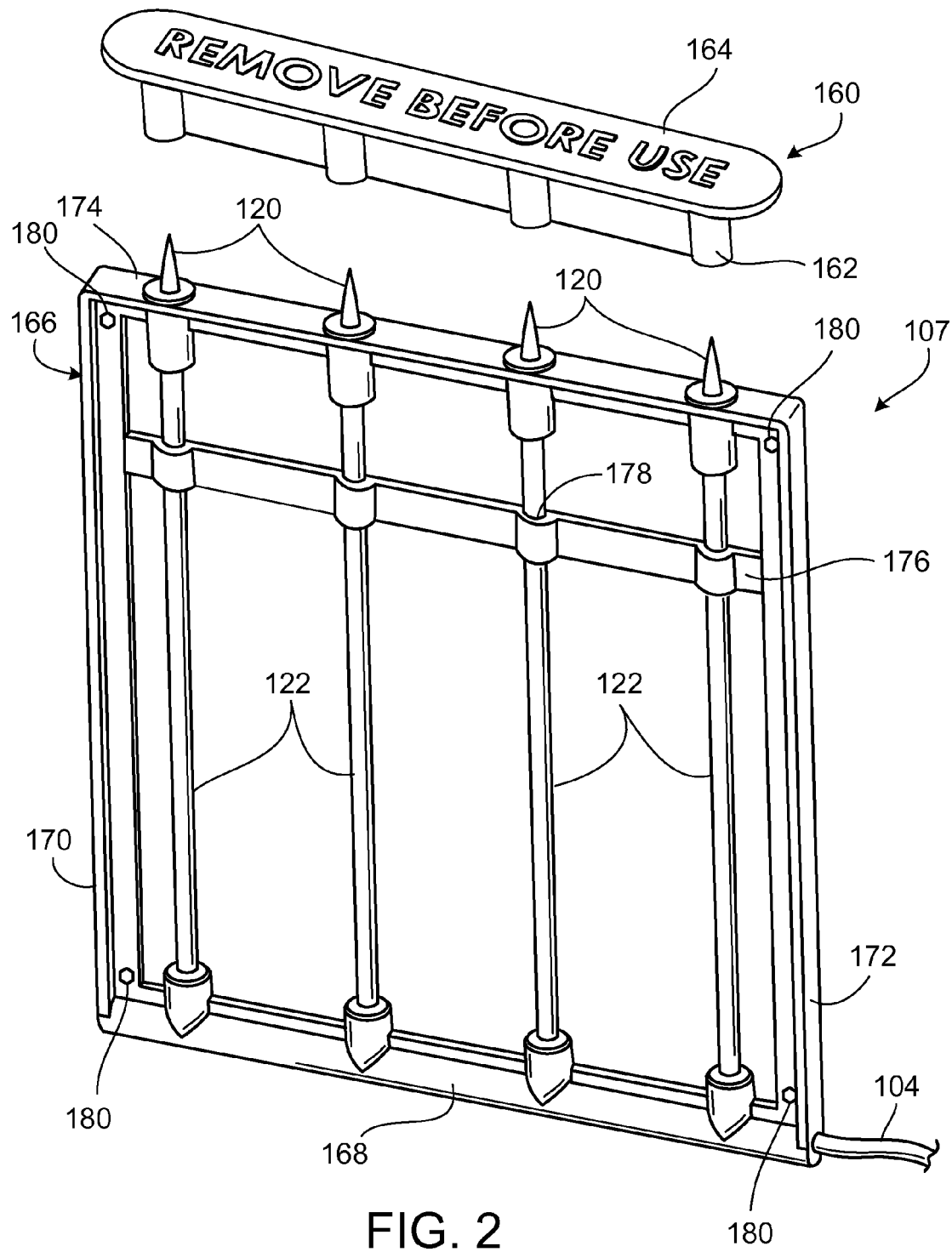
FIG. 2 is a perspective, exploded view of the drug administration fluid line cassette that is partially illustrated in FIG. 1 and a spike cover that is disposed over spikes of the drug administration fluid line cassette prior to use.

FIG. 2 illustrates the drug administration fluid line cassette 107 with a protective spike cover 160 removed from the spikes 120. As shown, feeder lines 122 are retained in a spaced apart configuration by a frame 166 of the cassette 107. The frame 166 includes along its bottom edge a manifold 168 that connect the feeder lines 122 to the drug delivery line 104, two side support members 170, 172 that extend from the manifold 168, and a top support member 174 that extends between the two side support members 170, 172. The side support members 170, 172 are attached (e.g., thermally bonded, adhesively bonded, or mechanically attached) at their bottom and top ends to the manifold 168 and top support member 174, respectively. The feeder lines 122 similarly extend between and are attached (e.g., thermally bonded, adhesively bonded, or mechanically attached) to the manifold 168 and top support member 174.

In addition to the frame 166, the cassette 107 includes a crossbar 176 that extends between the two side support members 170, 172. The crossbar 176 includes recessed regions 178 into which the feeder lines 122 are received and retained. In addition, hexagonal holes 180 are provided in the front surface of the cassette 107 (i.e., the surface of the cassette 107 that contacts the inner surface of a door 109 of the drug delivery device 103 when the cassette 107 is loaded in the cassette compartment of the drug delivery device 103). As described below, these holes 180 mate with hexagonal projections extending from the inner surface of the door 109 to secure the cassette 107 to the door 109 during use and to help ensure that only appropriate cassettes (e.g., cassettes intended for use with the drug delivery device 103 by the drug delivery device manufacturer) are used with the drug delivery device 103.

Still referring to FIG. 2, the spikes 120 are attached (e.g., thermally bonded, adhesively bonded, and/or mechanically attached) to and extend upward from the top support member 174 of the cassette 107. The drug vial spikes 120 can be formed of one or more relatively rigid medical grade plastics, such as polycarbonate or alphamethylstyrene (AMS), and the various fluid lines can be formed of a more flexible medical grade plastic, such as polyvinylchloride (PVC). Each of the spikes 120 can include, for example, a central channel that extends along the length of the spike and two openings (e.g., channels or slots) along the outer surface of the spike that lead to the central channel. The central channel of each spike is aligned with and fluidly connected to a vertical passage extending through the top support member 174.

The feeder lines 122 are in fluid communication with their associated spikes 120 via the vertical passages extending through the top support member 174. The feeder lines are also in fluid communication (via openings in the top surface of the manifold 168) with the central passage that extends through the manifold 168. The drug delivery line 104 is similarly connected to the manifold 168 and is in fluid communication with the central passage of the manifold 168. Thus, when the spikes 120 penetrate the rubber seals of the vials 116, 118 during use, drug can flow through the feeder lines 122, the manifold 168, the drug delivery line 104, and into the drip chamber 106.

The manifold 168, the side support members 170, 172, the top support member 174, and the crossbar 176 are typically formed of one or more materials that are more rigid than the material or materials from which the feeder lines 122 are made. Examples of such relatively rigid materials include polycarbonate and AMS. However, other relatively rigid materials can alternatively or additionally be used. Due to the construction and materials of the frame 166 and cross bar 176 of the cassette 107, the feeder lines 122 are held in substantially fixed positions relative to one another. As a result of this configuration, loading of the drug administration fluid line cassette 107 into the cassette compartment of the drug delivery device 103 is simplified.

Still referring to FIG. 2, the spike cover 160 is a unitary plastic structure that includes multiple tubular members 162 extending downward from an elongate structure 164. The tubular members 162 form cavities in which the drug vial spikes 120 of the cassette 107 are disposed prior to their insertion into the vials 116, 118. The cavities are sized and shaped so that the portions of the tubular members 162 forming those cavities grip their associated spikes 120 with sufficient force to prevent the cover 160 from falling off or being inadvertently knocked off the spikes 120 prior to loading the vials 116, 118 onto the spikes 120, while allowing the operator of the system to manually remove the cover 160 from the spikes 120 at the desired time. The spike cover 160 is removed from the spikes 120 of the cassette 107 prior to loading the vials 116, 118 onto the spikes 120.

Referring again to FIG. 1, which illustrates the cassette 107 in the cassette compartment of the drug delivery device 103, the spikes 120 of the cassette 107 have been inserted into the vials 116 and 118, which are retained in vial holders 112 and 114, respectively. Peristaltic pumps 132 extend from the inner face of the drug delivery device 103 and align with the feeder lines 122 (between the cross bar 176 and the manifold 168 of the cassette 107) such that when one of the pumps 132 is operated, the drug is drawn from the vial 116, 118 associated with that pump and delivered via the feeder lines 122, the manifold 168, and the drug delivery line 104 to the drip chamber 106 of the blood circuit.

Each of the feeder lines 122 passes through (e.g., is threaded through) a fluid detector 128, arranged in a spaced configuration across the inner face of the drug delivery device 103 above the peristaltic pumps 132. The fluid detectors 128 are capable of detecting air bubbles within the feeder lines 122. As a result, each of the fluid detectors 128 can determine whether its associated drug vial 116, 118 is empty during treatment, because air is drawn from the vial 116, 118 into the feeder line 122 when the vial is empty.

In some implementations, the fluid detectors 128 are ultrasonic detectors. The AD8/AD9 Integral Ultrasonic Air-In-Line, Air Bubble Detector (manufactured by Introtek International (Edgewood, N.Y.)), for example, can be used. Other ultrasonic sensors, such as the BD8/BD9 Integral Ultrasonic Air Bubble, Air-In-Line & Liquid Level Detection Sensors (also manufactured by Introtek International) can also be used. Similarly, other types of sensors, such as optical sensors, can be used as the fluid detectors. Examples of such sensors include the OPB 350 fluid detector made by Optek. Other types of optical detectors can alternatively or additionally be used.

In some implementations, the fluid detector 128 includes a sensor that, in addition to sensing the presence of an air bubble within its associated feeder line 122, can sense the presence of the feeder line itself. In some implementations, the diameter of the feeder line is too small for currently available sensors to reliably detect the presence of the feeder line.

The operations of the fluid detectors 128 can be directed by the control unit of the drug delivery device 103. For example, the control unit may activate and deactivate the fluid detectors and process information provided by the fluid detectors. In some implementations, the fluid detectors send signals indicative of the presence or absence of fluid in the feeder lines 122 to the control unit. The control unit then determines, based in part on the signals received from the fluid detector, whether to raise an alert and/or alarm, as described below with respect to FIGS. 6-8.

Figure 3:
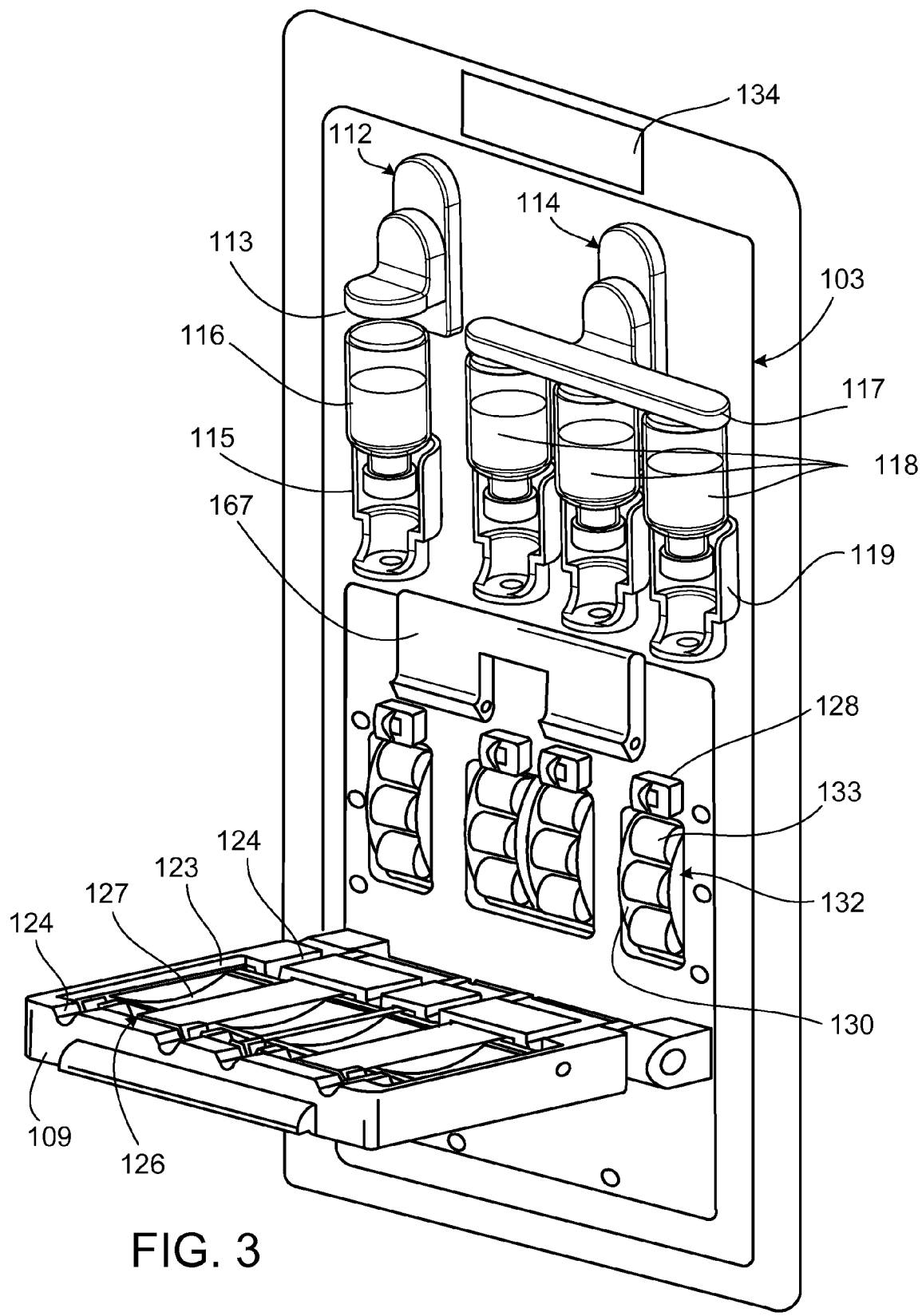
FIG. 3 is a perspective view of the hemodialysis machine of FIG. 1 with the door of the drug delivery device opened.

FIG. 3 illustrates the drug delivery device 103 with the door 109 opened and the drug administration fluid line cassette 107 removed. As shown, the inner surface of the door 109 includes a recessed region 123 that is configured to receive the rigid frame 166 of the cassette 107 and elongate slots 124 that are configured to receive the feeder lines 122 of the cassette 107 without substantially deforming the feeder lines 122. In certain implementations, the recessed region 123 and slots 124 are sized so that the frame 166 and feeder lines 122 of the cassette 107 can be snapped into the recessed region 123 and slots 124, respectively, and thus releasably secured to the door 109. The inner surface of the door 109 also includes the hexagonal projections that are configured fit into the hexagonal holes 180 formed in the cassette 107 when the cassette 107 is loaded into the door 109. The hexagonal projections can be sized and shaped to create a snap fit or a snug press fit that secures the drug administration fluid line cassette 107 to the door 109.

In addition, the inner surface of the door 109 includes spring-loaded members 126 that define recesses or raceways 127 that receive roller members of the peristaltic pumps 132 of the drug delivery device 103 when the door 109 is closed. Springs are connected to top and bottom regions of each member 126 and to an internal fixed member in the door 109 to allow the members 126 to flex in response to contact with the rollers of the peristaltic pumps 132 or in response to contact with the feeder lines 122 positioned between the members 126 and the rollers of the peristaltic pumps 132.

Still referring to FIG. 3, the peristaltic pumps 132 are positioned in a spaced configuration across the face of the drug delivery device 103. Each pump 132 includes multiple rollers 133 that compress the associated feeder line 122 in a manner to create a "pillow" of fluid (i.e., a "pillow" of air or liquid) that is pinched between two points of the feeder line 122 that are compressed by the pump rollers 133. The rollers 133 are arranged around a circumference of a rotatable frame. As the frame is rotated, the rollers 133 force the "pillow" of fluid through the feeder line 122 to the drug delivery line 104. The peristaltic pumps 132 are configured to rotate about an axis that extends in a direction that is substantially parallel to the face of the drug delivery device 103. When the cassette 107 is positioned in the cassette compartment between the inner face of the drug delivery device 103 and the closed door 109, the feeder lines 122 align with the pumps 132 and are thus pressed into the raceways 127 of the spring-loaded members 126 in the door 109. The spring force provided by the springs of the spring-loaded members 126 helps to take up tolerance between the raceways 127 and the rollers 133, and thus helps to ensure that a fixed compression force is applied to the feeder lines positioned between the raceways 127 and the rollers 133.

During operation of the pump 132, the rollers 133 are rotated from top to bottom (in the view shown in FIG. 3) and thus force pillows of fluid downward through the associated feeder line 122. When the pump 132 is being operated, vacuum pressure is applied to the drug vial 116, 118 that is connected to the feeder line 122. In certain cases, the initial pressure in the drug vial 116, 118 is equal to the ambient pressure, and when all of the drug has been delivered, the ending pressure within the vial is less than ambient pressure (e.g., about −10 psi). In other words, the pressure within the drug vial 116, 118 progresses from ambient to the negative pressure as the drug is delivered. The pump 132 is configured to generate a vacuum pressure within the feeder line 122 that exceeds the competing vacuum within the drug vial 116, 118. As a result, the drug is drawn from the vial 116, 118, through the drug vial spike 120 and into the feeder line 122.

The spacing of the rollers 133 about the circumference of the rotatable frames 130 of the peristaltic pumps 132 is selected so that at least one of the rollers 133 is positioned in the raceway 127 of the associated spring-loaded member 126 when the door 109 of the drug delivery device 103 is closed. This helps to ensure that the feeder lines 122 positioned between the pumps 132 and the raceways 127 are always occluded in at least one location and thus helps to prevent the drugs from passing through the feeder lines 122 to the manifold 168 when the pumps 132 are not in operation.

Referring again to FIGS. 1-3, the drug vial holders 112, 114 of the drug delivery device 103 can be equipped with various types of sensors for sensing the presence of a vial, identifying the type of drug vial installed, detecting the size of the drug vials, and/or detecting the mass of the drug vials. In some implementations, each drug vial holder 112, 114 includes a sensor to sense the presence of a vial or drug container. In certain implementations, each drug vial holder 112, 114 includes a system which identifies the drug vial installed. The drug vial identification system can, for example, include a bar code reader that reads bar codes on the vials. Different types of sensors can alternatively or additionally be used. In some implementations, for example, the vial identification system uses RFID technology. Other examples of suitable sensors include color sensors for sensing the color of color-coded drug vials and/or for sensing the color of the drug within the vial, photo sensors (e.g., cameras) that are equipped with text recognition software to read text on the drug vial, capacitive sensors that permit different size vials to be detected, load cells or scales that detect the mass of the vial, and conductivity or electrical impedance sensors that can be used to determine the type of drug within the vial.

The sensors can communicate with the control unit, sending detected information to the control unit and receiving commands from the control unit. The control unit can also control the pumps 132 to ensure that only one of the pumps 132 is in operation at a time. This helps to ensure that drug is pulled from only one of the vials 116, 118 at a time during treatment. Upon determining that the prescribed volume of the drug has been delivered (based on monitoring the operation of the pumps 132), the control unit can turn off the pump 132 associated with that drug vial 116, 118 and turn on the pump 132 associated with the drug vial 116, 118 containing the next drug to be delivered. In addition, after the full contents of a vial have been evacuated, air will be sucked into the feeder line 122 associated with that vial and will be detected by the fluid detector 128. In response, the control unit can turn off the pump 132 associated with the empty vial and turn on the pump 132 associated with the vial containing the next drug to be delivered.

The control unit can also control certain components of the drug delivery device 103 based on signals received from the drug vial ID sensors, which indicate the presence of a vial and/or the identity of the vial contents. Such an arrangement can help to ensure that the correct vials (e.g., the correct number of vials and the vials containing the correct contents) are used for the treatment. Upon receiving signals from the drug vial ID sensors that do not match the inputted treatment information, for example, an alarm (e.g., an audible and/or visual alarm) can be activated. Alternatively or additionally, the drug delivery device 103 can be configured so that treatment cannot be initiated until the sensors detect the correct combination of vials.

The drug delivery device 103 (e.g., the control unit of the drug delivery device 103) is configured to sense if the blood pump 108 of the dialysis machine 101 is running and to pause drug delivery if the blood pump 108 is stopped. This technique prevents "pooling" of the delivered drug in the drip chamber 106 during treatment.

Still referring to FIGS. 1-3, the drug delivery device 103 further includes a user interface 134 that is connected to the control unit. The user interface 134 includes keys that allow the user to navigate through displays associated with the vials 116, 118 and set the desired dosage for each of the vials 116, 118. In addition, the user interface 134 includes start and stop keys that allow the user to start and stop the drug delivery device 103.

Any of various other types of user interfaces can alternatively or additionally be used. In some implementations, the drug delivery device includes a user interface that allows the user to select a drug to infuse from a menu. In certain implementations, the user may confirm that the drug identified by the drug vial ID sensor is correct and/or make appropriate adjustments. The user interface can be used to input and/or monitor various different treatment parameters. Examples of such parameters include drug dosage, drug delivery rate, amount of drug delivered, status of the drug delivery for each drug channel, time, percent complete, percent remaining, time remaining, time delivered, date, patient ID, patient name, alarms, alerts, etc. Such user interfaces can include a color graphical display. In certain implementations, for example, the user interface is color coded according to drug, dosing, or status of drug delivery (e.g., done, running, ready, etc.).

The hemodialysis machine 101 also includes an alarm and/or alert system to which the control unit of the hemodialysis machine 101 is connected. The alarm and/or alert system can be configured to emit a visual and/or audio alarm and/or alert. The alarm and/or alert system can further include pre-programmed alarm and/or alert limitations so that when a user modifies any aspect of the system to be outside of the limitations, or the machine itself detects any aspects of the system to be outside of the limitations, the module emits an alarm and/or alert.

Still referring to FIGS. 1-3, a method of using the hemodialysis system 100 to perform hemodialysis on a patient will now be described. Prior to beginning hemodialysis treatment on a patient, the various lines that make up the blood circuit and dialysate circuit of the hemodialysis machine are primed, and then the patient lines 105 are connected to the patient. After connecting the patient lines 105 to the patient, the blood pump 108 is activated to circulate blood through the blood circuit. A dialysate pump is also activated to pump dialysate through the dialysate circuit of the hemodialysis machine. The blood is drawn from the patient and delivered to the drip chamber 106 via the arterial patient line. The drip chamber 106 acts as an air trap such that any air in the blood is released as the blood passes through the drip chamber 106. In particular, the drip chamber 106 includes a vent through which air released from the blood can be vented from the drip chamber 106. The blood is then pumped from the drip chamber 106 to the dialyzer 110, which includes a semi-permeable membrane that divides the dialyzer 110 into two chambers. As the blood passes through one of the chambers of the dialyzer 110, dialysate from the dialysate circuit passes through the other chamber. As the blood flows by the dialysis fluid, impurities, such as urea and creatinine, diffuse through the semi-permeable membrane into the dialysate. The spent dialysate is either disposed of or recycled and reused. The cleansed blood exiting the dialyzer 110 is returned to the patient via the venous patient line.

After initiating the hemodialysis treatment, the operator of the hemodialysis system 100 (e.g., the physician, nurse, medical assistant, or patient) determines the prescribed Epogen® dose and then consults a dosing schedule for the different vial combinations that can be used to deliver the prescribed Epogen® dose. Examples of dosing schedules are described in U.S. patent application Ser. No. 12/827,119, which is herein incorporated by reference in its entirety. The operator then selects one of the Epogen® vial combinations provided based on the operator's preference and loads the selected Epogen® vials into the drug vial holders. The operator also loads a vial of Venofer® into one of the drug vial holders. In some implementations, the operator selects from various Venofer® vials that are the same size but contain different amounts of Venofer®.

The operator of the system then connects the disposable drug administration fluid line cassette 107 to the inner surface of the door 109 by inserting the frame 166 and feeder lines 122 into their corresponding recessed regions 123 and slots 124. As a result of this, the hexagonal shaped projections that extend from the inner surface of the door 109 slide into the matching holes 180 formed in the frame 166 of the drug administration fluid line cassette 107. The mating engagement of the hexagonal shaped projections and openings 180, along with the snap fit of the cassette frame 166 and feeder lines 122 into their corresponding recessed regions 123 and slots 124, helps ensure that the cassette 107 remains securely fixed to the door 109. In addition, the unique hexagonal shape of the projections and openings 180 can help to ensure that only drug administration fluid line cassettes intended for use with the drug delivery device 103 can be used. For example, drug administration fluid line cassettes that do not include holes capable of receiving the hexagonal projections of the door 109 could not be properly secured to the door 109. This would indicate to the operator that an incorrect cassette was loaded into the cassette compartment of the drug delivery device 103 and, in many cases, will prevent the door 109 from shutting and thus prevent the drug delivery device 103 from being operated with that cassette.

After loading the drug administration fluid line cassette 107 onto the door 109, the operator closes the door 109 and secures a latch 167 to hold the door 109 in the closed position. Because the cassette 107 is securely fastened to the door 109 in a desired position, the feeder lines 122 align with their associated pumps 132 and fluid detectors 128 when the door 109 is closed. Thus, as the door 109 is closed, the protruding peristaltic pumps 132 press the feeder lines 122 into the raceways 127 formed along the inner surface of the door 109, and the inner surface of the door 109 presses the feeder lines 122 into engagement with the fluid detectors 128. With the door 109 in the closed position, the spikes 120 of the cassette 107 rest directly below the holes formed in the bottom members 115, 119 of the vial holders 112, 114.

The prescribed dosages of Venofer® and Epogen® are then entered into the drug delivery device 103 using the user interface 134 of the hemodialysis machine 101 with which the control unit of the drug delivery device 103 is in communication. Alternatively or additionally, the prescribed dosage of Venofer® and Epogen® can be electronically transmitted to the control unit of the drug delivery device 103 from a device, such as a portable computing device, or from a database or website accessible by the patient's prescribing physician. The operator, after reviewing the prescribed dosage entered into or transmitted to the machine, confirms that the prescribed dosage is correct by pressing a button (e.g., an "Accept" or "Confirm" button) on the user interface 134 of the hemodialysis machine 101, which initiates the spiking and priming process.

Figure 4:
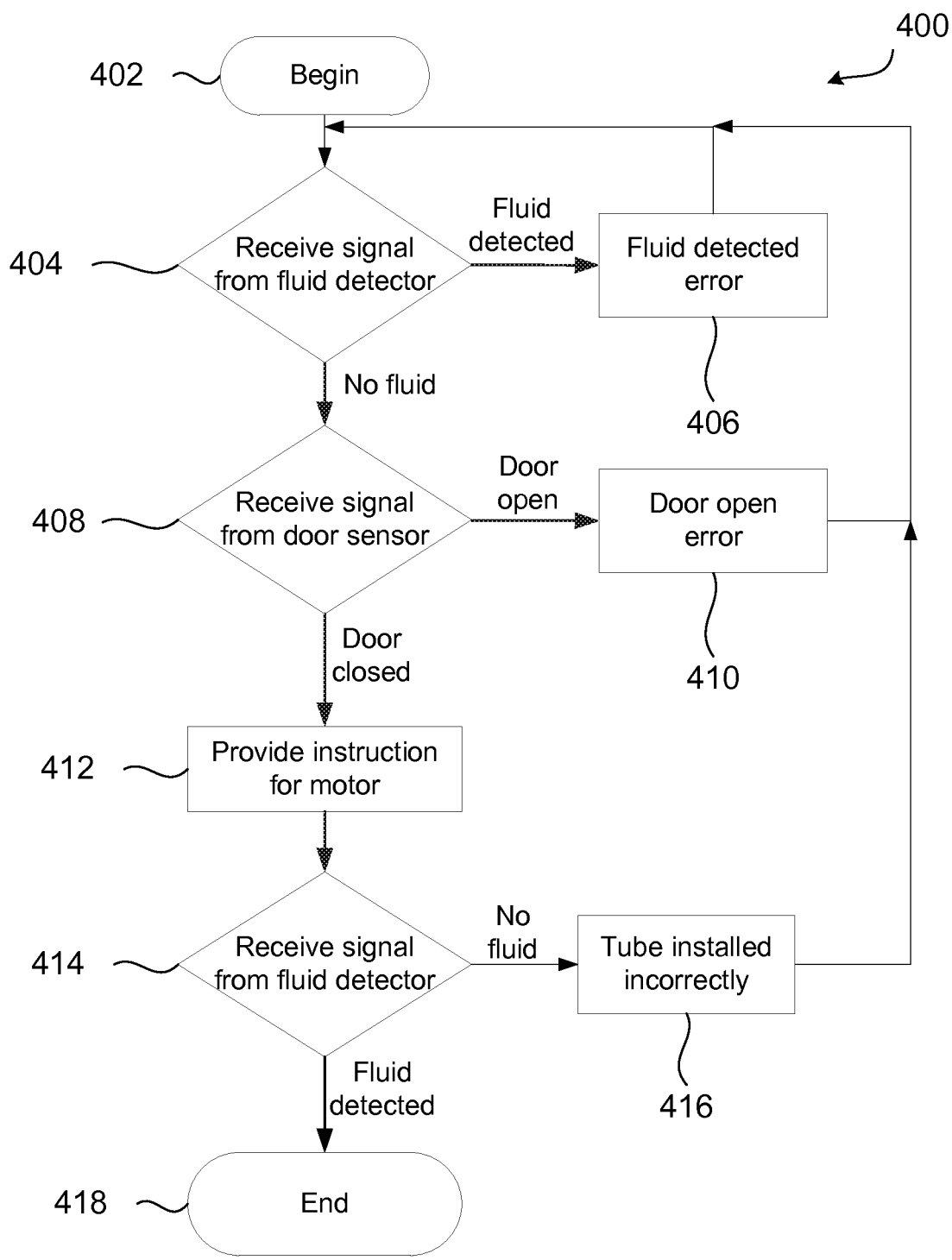
FIGS. 4 and 5 are flow charts depicting methods of detecting fluid line or fluid tubing installation.

Referring also now to FIG. 4, after spiking the vials 116, 118, the machine determines whether the feeder lines 122 have been properly installed. The process (400) for determining whether the feeder lines 122 have been properly installed installation begins (402) and a signal from the fluid detector 128 is received (404) by the control unit. If the received signal indicates fluid detected, the system provides a fluid detected error (406). The fluid detected error can be an alert or an alarm provided by the system. The fluid detected error can be a result of wet feeder lines 122, for example, if there is moisture on the outside of the feeder lines 122. The fluid detected error can also be a result of an oversensitive fluid detector 128. The operator can check to ensure there is no moisture or fluid on or in the feeder lines 122 and restart the process 400. If the fluid detected error still triggers, the fluid detector 128 may be oversensitive or faulty and need replacement. By receiving a signal from the fluid detector 128 before fluid is pumped from the vials 116, 118, the fluid detector 128 can be calibrated or checked for proper functioning. One advantage of checking for proper functioning of components prior to pumping fluid from the vials 116, 118 is that problems can be addressed without wasting any drug.

If the signal received from the fluid detector 128 indicates no fluid, a signal is received from a door sensor (408) by the control unit. The door sensor is a sensor on the door 109 or the latch 167 of the door 109 that detects whether the door 109 is properly closed. If the signal received from the door sensor indicates the door 109 is open, the system provides a door open error (410). The door open error can be an alert or an alarm provided by the system. The operator can ensure there are no obstructions (such as the feeder lines 122) preventing the door from closing properly. Once the door 109 is properly closed, the operator can continue or restart the process 400.

If the signal received from the door sensor indicates the door is properly closed, an instruction is provided by the control unit for a motor (412) of the pump 132. The instruction directs the motor to pump the drug from the vial fluidly connected to the pump 132. By activating the pumps 132, either sequentially or simultaneously, the feeder lines 122 of the drug administration fluid line cassette 107 are primed, causing a portion of the drug to be drawn from each of the vials 116, 118. After a period of time passes after providing the instruction, a signal is received by the control unit from the fluid detector 128 (414). The period of time can be a period of time required under normal operating conditions for the feeder lines 122 to be primed, or for the drug to reach the pump 132. If the signal received from the fluid detector 128 at this point indicates no fluid detected in the feeder line 122, it is determined that the tube is installed incorrectly (416). The system can provide an alarm or alert to indicate an incorrect tubing installation to the user. If the signal received from the fluid detector 128 indicates fluid is detected, then the tubing is correctly installed and the process can end (418) and the pump 132 is stopped and pinches off or occludes the feeder line 122.

After priming the feeder lines 122, Venofer® is delivered from the Venofer® vial 116 to the drip chamber 106 by activating the pump 132 associated with the Venofer® vial 116 (while leaving all of the other pumps off). The pump 132 delivers all of the Venofer® in the vial 116 unless an error is detected. A possible error that can be detected is the incorrect installation of the tube, for example, by the process (500) depicted in FIG. 5.

Figure 5:
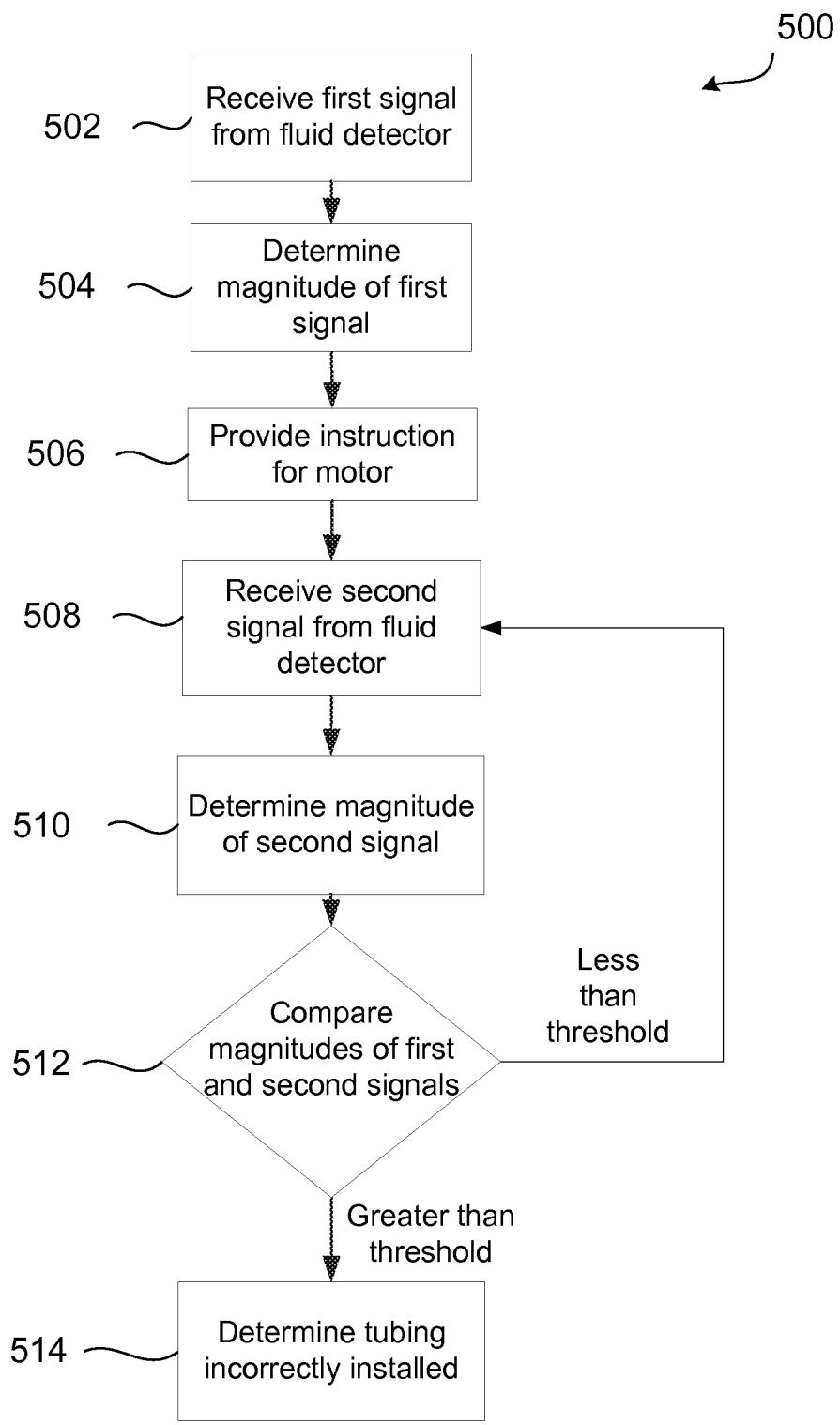

Still referring to FIG. 5, while delivering the Venofer® to the drip chamber 106 via the feeder line 122, the control unit receives a first signal from the fluid detector (502). The first signal can be received after the priming of the feeder lines 122. The first signal is a signal indicating the presence of fluid in the tube. For example, a voltage magnitude of the signal (e.g., greater than 0.05 volts peak to peak when measured directly from the receive element) can indicate that fluid is present. The magnitude of the first signal is determined (504) and stored. The magnitude of the first signal is used as a baseline measurement against which later signals are measured. Using the magnitude of the first signal to compare later signals, rather than a fixed, or even adjustable, predetermined magnitude can allow for discrepancies between different fluid detectors 128 and drug delivery devices 103.

Instruction for the motor to pump (or continue pumping) the drug is provided (506) by the control unit. The instruction is provided to the motor to pump the drug for delivery of the drug to the patient. A second signal is received from the fluid detector (508). The second signal is received at a time later than the first signal. The pump 132 is active during the time between the first and second signals, as the instruction is provided to the motor. A magnitude of the second signal is determined (510).

The magnitudes of the first and second signals are compared (512). If the difference between the two signals is greater than a threshold amount or greater than or equal to the threshold amount, the tubing is incorrectly installed (514). For example, in some implementations, an amplified and filtered signal presented to an A/D voltage difference of between 0.250-0.500V can be used as the threshold amount. With an incorrectly installed tubing, such as a tubing occluded by the door 109 of the drug delivery device 103 improperly closed on the tubing, the fluid is unable to properly flow through the tubing. With an occlusion in the tubing, the fluid builds up at the point of occlusion, which can result in an expansion of the tube at the point of occlusion and an increased volume of fluid in the tube. The increased volume of fluid can result in a signal from the fluid detector 128 that is greater than a normal range. Thus, incorrectly installed tubing can be determined by a second signal with a magnitude greater than a first signal by a threshold amount.

If the magnitude of the second signal is not greater than the magnitude of the first signal, the control unit can continue to receive signals for comparison. The comparisons can continue to be made to the first signal, or alternatively, the second signal can be used as a new baseline measure. In some implementations an average or other combination of the magnitudes of the first and second signals can be used. In some implementations, one of the two signals is chosen by some criteria as the baseline measurement. For example, the signal with the lower magnitude can be used for future comparisons. The comparisons can continue throughout the drug delivery process, or only for a certain period of time during the delivery.

The pump associated with the first Epogen® vial 118 (i.e., the Epogen® vial directly to the right of the Venofer® vial 116) is then activated such that Epogen® is delivered to the drip chamber 106. A similar process as described above can be used to determine whether the feeder line 122 associated with the first Epogen® vial is properly installed. After confirming proper installation, Epogen® is pumped. When the fluid detector 128 detects air in the feeder line 122, a signal is sent to the control unit, indicating that the first Epogen® vial 118 is empty. The control system then sends a signal causing the pump associated with the first Epogen® vial 118 to be turned off after assuring that an additional known volume is pumped so that the Epogen® in the line downstream of the fluid detector 128 is flushed down to a segment where the delivery of drug from the next vial can push that Epogen® remaining in the line to the drip chamber 106. In particular, the control unit ensures that the additional pumped volume is sufficient to push the Epogen® past the pump 132 and into the passage of the manifold 168 such that the next volume of drug delivered will push the Epogen® to the drip chamber 106. The control unit also sends a signal to activate the pump 132 associated with the second Epogen® vial 118 (i.e., the Epogen® vial directly to the right of the first Epogen® vial). The Epogen® delivery process described above is then repeated for the second and third Epogen® vials.

After delivering the desired amounts of Venofer® and Epogen® to the drip chamber 106, the drug delivery device 103 is deactivated and the drug administration fluid line cassette 107 and vials 116, 118 are removed from the drug delivery device 103 and discarded.

Each of the fluid detectors 128 can be part of a fluid detection system that is configured to determine if any of the vials 116, 118 are empty by analyzing the presence or absence of fluid in the feeder tubes 122.

Figure 6:
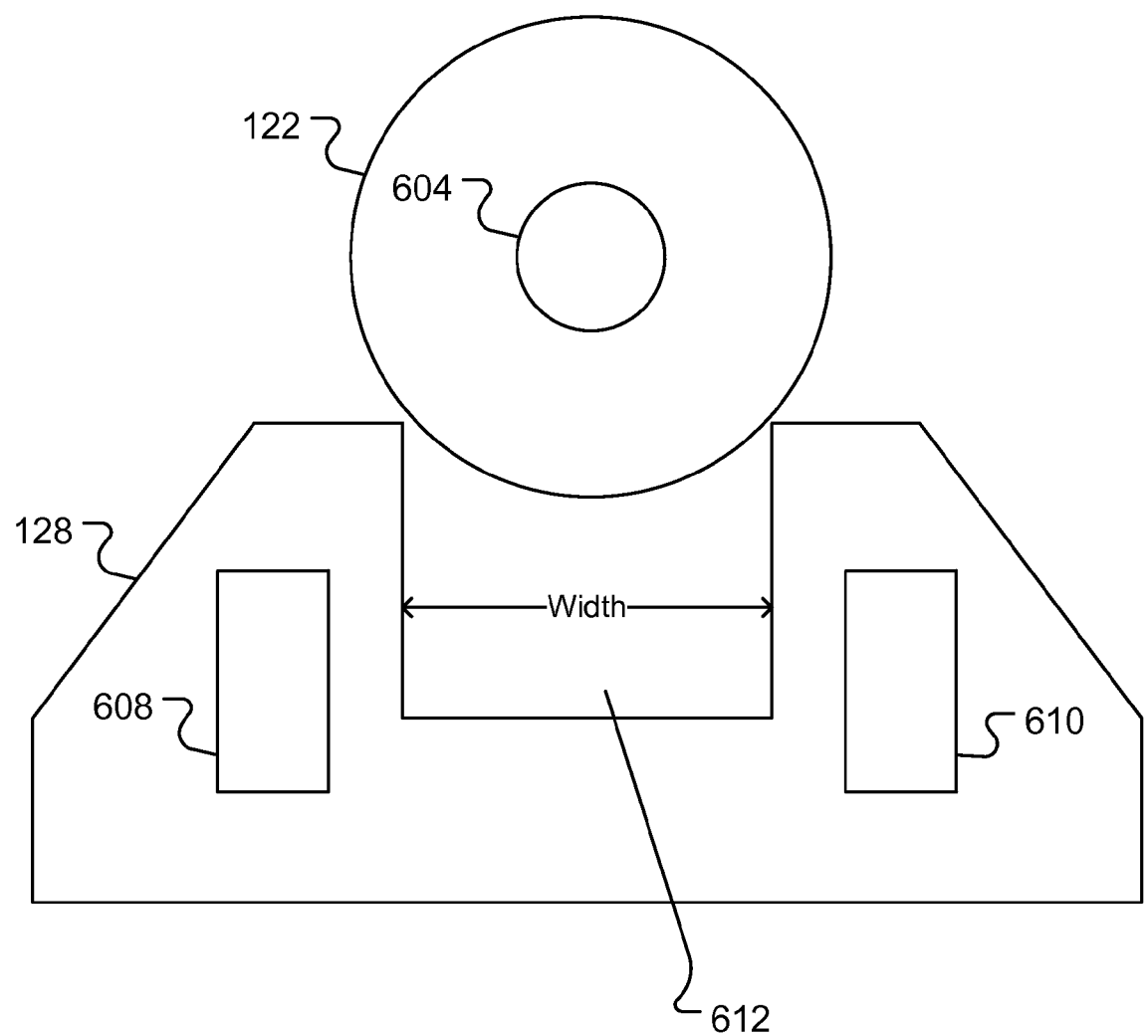
FIG. 6 illustrates a cross sectional view of one or the feeder lines being inserted into a central cavity of one the fluid detectors.

FIG. 6 illustrates a cross sectional view of one or the feeder lines 122 being inserted into a central cavity of one the fluid detectors 128. A feeder line 122 is placed adjacent to a fluid detector 128. The feeder line 122 typically has an outer diameter of less than or equal to 0.25 inch. For example, the feeder line 122 may have an outer diameter of 0.125 inch plus or minus 0.003 inch. The feeder line 122 typically has an inner diameter 604 of less than or equal to 0.05 inch. For example, the feeder line 122 may have an inner diameter of 0.03 inch plus or minus 0.001 inch.

The fluid detector 128 includes the cavity 612 which allows the feeder line 122 to be positioned between an ultrasonic sensor transmitter 608 and an ultrasonic sensor receiver 810. The cavity 612 in the fluid detector 128 for the feeder line 122 may be smaller than the outer diameter of the feeder line 122 so that the medical fluid tube must be deformed in order to fit into the allotted space. For example, the outer diameter of the feeder line 122 may be about 0.025 inch greater than the width of the cavity 612. In some implementations, the outer diameter of the feeder line 122 is about 0.125 inch and the width of the cavity 612 is about 0.1 inch.

When the feeder line 122 is inserted into the cavity 612 of the fluid detector 128, the relative size of the cavity 612 and the feeder line 122 causes a distortion in the shape of the feeder line 122. The distorted feeder line 122 applies pressure to the fluid detector 128 and the pressure holds the feeder line 122 in position.

The ultrasonic sensor transmitter 608 and the ultrasonic sensor receiver 610 are positioned within the housing of the fluid detector 128. Ultrasonic signals are transmitted from the ultrasonic sensor transmitter 608 and are received by the ultrasonic sensor receiver 610. The presence of fluid in the interior 604 of the feeder line 122 can be determined based on the strength of the ultrasonic signal received by the ultrasonic sensor receiver 610. The ultrasonic sensor receiver 610 transforms the ultrasonic signal into voltage. The resulting voltage will be higher when fluid is present in the feeder line 122 and lower when it is not.

The ultrasonic signal being transmitted from the ultrasonic sensor transmitter 608 to the ultrasonic sensor receiver 610 can cause cavitation, the formation of small bubbles within the fluid in the feeder line 122. The accumulation of these air bubbles can affect the transmission of the ultrasonic signal through the feeder line 122 and consequently affect the voltage provided by the ultrasonic sensor receiver 610, as described below.

Figure 7:
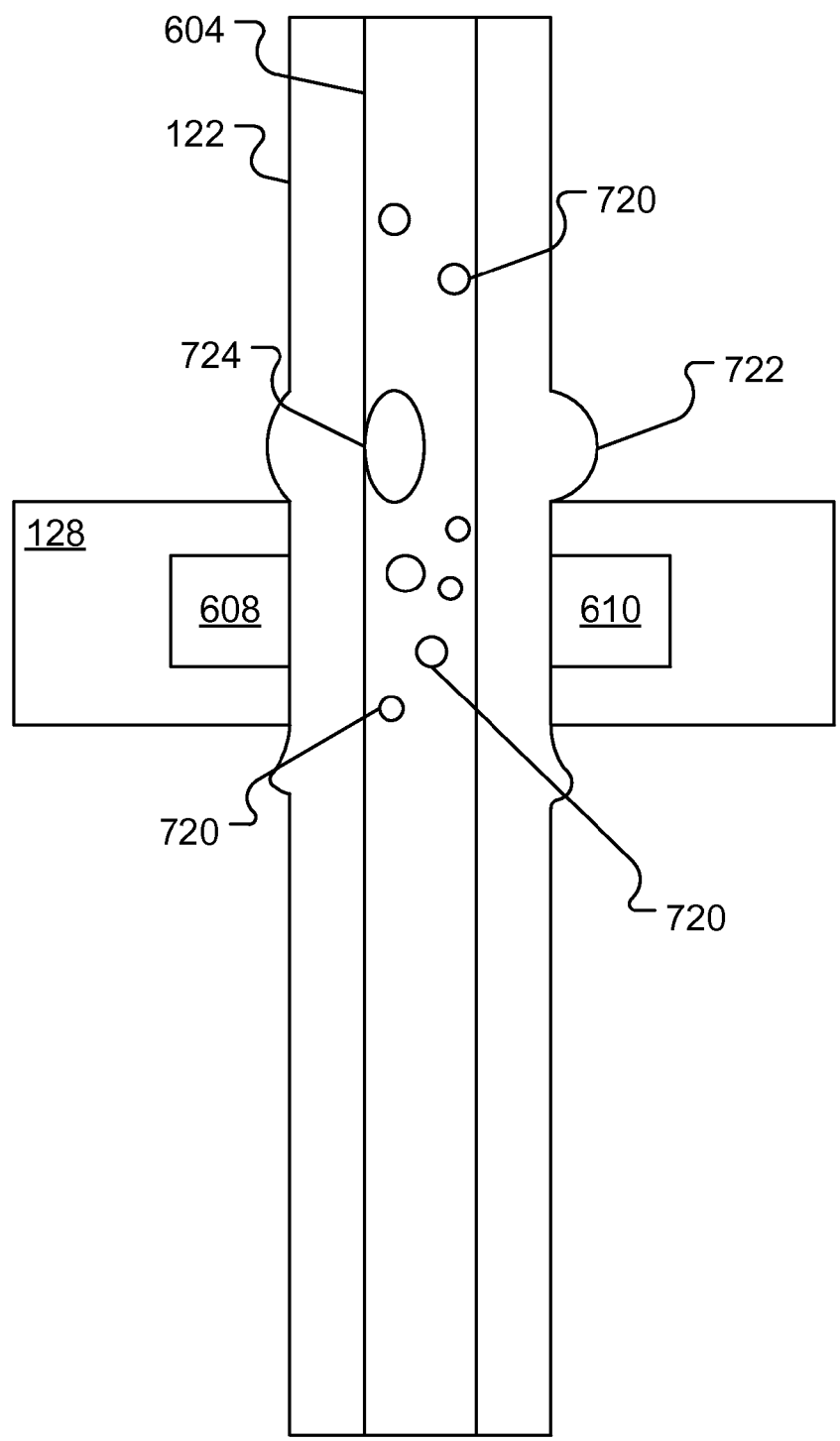
FIG. 7 is a schematic illustration of the fluid detector being used to detect air in the feeder line.

FIG. 7 is a schematic illustration of the fluid detector 128 being used to detect air in the feeder line 112. As discussed above, inserting the feeder line 122 into the fluid detector 128 can cause a distortion in the medical fluid tube 122.

As the ultrasonic sensor transmitter 608 continuously transmits ultrasonic energy through the feeder line 122, the ultrasonic energy can cause the formation of air bubbles 720 (i.e. cavitation) within the fluid in the interior 604 of the feeder line 122. The air bubbles 720 tend to accumulate and form an air pocket 724 between the ultrasonic sensor transmitter 608 and the ultrasonic sensor receiver 610.

As more air accumulates in the feeder line 122, the voltage provided by the ultrasonic sensor receiver 610 in response to the ultrasonic energy received from the ultrasonic transmitter 608 declines. This decline makes it difficult to determine if medical fluid is flowing through the feeder line 122. For example, a low voltage reading may be caused by a collection of air bubbles caused by cavitation or may be caused by the absence of fluid in the medical fluid tube.

To mitigate cavitation in the feeder line 122, the ultrasonic sensor transmitter 608 can be repetitively activated to reduce (e.g., minimize) the accumulation of air bubbles within the feeder line 122. For example, the ultrasonic sensor transmitter 608 can be active for 5 ms and inactive for 995 ms. The ultrasonic transmitter can alternatively be active for other periods. For example, the ultrasonic sensor may be active for a period of 2-15 ms and subsequently inactive for 998 to 985 ms. A reading can be taken from the ultrasonic sensor receiver 610 at any point during which the ultrasonic sensor transmitter 608 is transmitting. In some implementations, a reading is taken near the end of the transmission by the ultrasonic sensor transmitter. For example, a reading may be taken from the ultrasonic transmitter receiver 610 4 ms into a 5 ms transmission by the ultrasonic sensor transmitter 608.

The effect of cavitation can be further mitigated by taking multiple readings before determining there is a lack of fluid in the feeder line 122 and transmitting a signal to that effect. For example, the system may not signal a lack of fluid in the feeder line 122 until fluid has been absent for three consecutive seconds.

Figure 8:
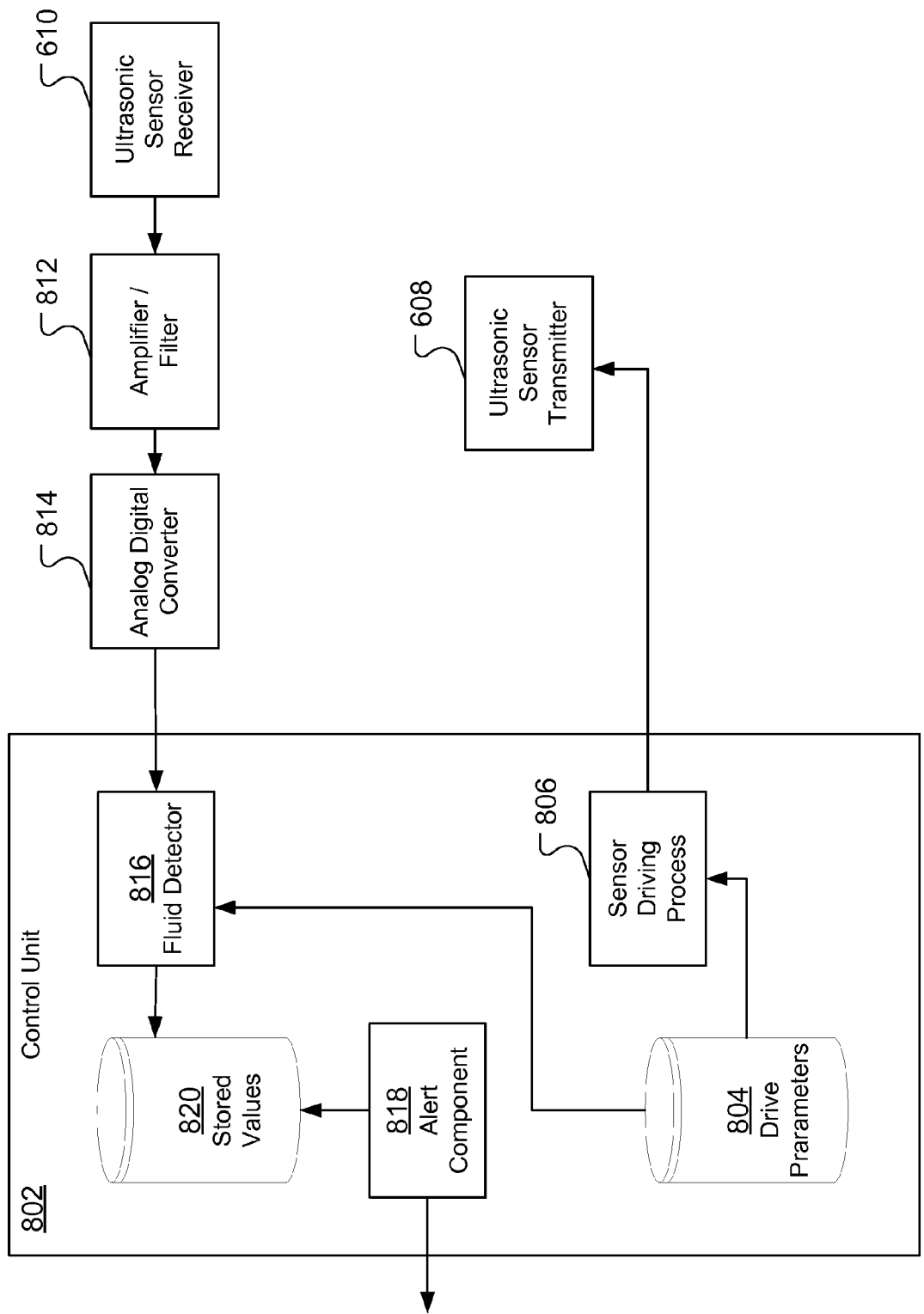
FIG. 8 illustrates an example of a fluid detection system.

FIG. 8 illustrates an example of a fluid detection system. A control unit 802 can include a set of drive parameters 804. The drive parameters 804 can be stored in persistent memory (for example, flash memory or magnetic storage) or can be stored in volatile memory such as random access memory. The drive parameters 804 specify operations of the fluid detection system. For example, the drive parameters 804 can specify a period during which an ultrasonic sensor transmitter 608 is to transmit (transmit time), a period of time the ultrasonic sensor transmitter is to wait until the next transmission (wait time), a time when a reading is to be taken from the ultrasonic sensor receiver (read time), and a threshold value which is used to determine if fluid is detected.

The transmit time and the wait time defines a duty cycle. For example, the duty cycle can be 1 second long. The read time may be defined relative to the transmit time or the duty cycle.

Based on the parameter values, the control unit 802 causes the sensor driving process 806 to send a signal to the ultrasonic sensor transmitter 608. In some implementations, the signal is a 2.5 Mhz drive signal. The ultrasonic sensor receiver element 610 receives a signal transmitted by the transmitting ultrasonic sensor 608. The signal is amplified and filtered 812 to produce a clear signal. The clear signal is converted to a digital signal using an analog digital converter 814.

The fluid detector 816 receives the digital signal. At the time specified by the drive parameters 804, the fluid detector 816 compares the value of the digital signal to a threshold value to determine if fluid is detected. In some implementations, the fluid detector determines if fluid was detected during the previous cycle. If fluid was detected during the previous cycle, the fluid detector compares the digital signal to a first threshold value. If fluid was not detected, the fluid detector compares the digital signal to a second threshold value. For example, if fluid was previously detected, the fluid detector may determine that fluid is not currently detected if the digital signal is below 2050 mV. If fluid was not previously detected, the fluid detector may determine that fluid is not currently detected if the digital signal is below 2100 mV. In some implementations, the thresholds are calibrated based on experimental performance of the ultrasonic sensors. The fluid detector stores the most recently received signal in an internal register.

Intermittently, the fluid detector determines whether or not fluid is detected during the most recent duty cycle, the fluid detector stores the value in a stored value repository 820. The stored value repository can maintain a number of historic readings. For example, the stored value repository may store an indicator of the last 3, 4, 5, or 6 stored values.

An alert component 818 signals an alert and/or alarm condition if all of the historic readings in the stored values repository 820 indicate that no fluid was detected. For example, if no fluid is detected every 500 ms for 3 seconds (for a total of six readings), then the alert component 818 signals the alert and/or alarm condition. By waiting until no fluid has been detected in the feeder line 122 for 3 seconds, the number of false alarms are reduced. For example, a small air bubble passing through the feeder line 122 will not trigger an alert or alarm. The alarm alerts an operator if the vials are empty of medical fluid and need to be replaced.

Figure 9:
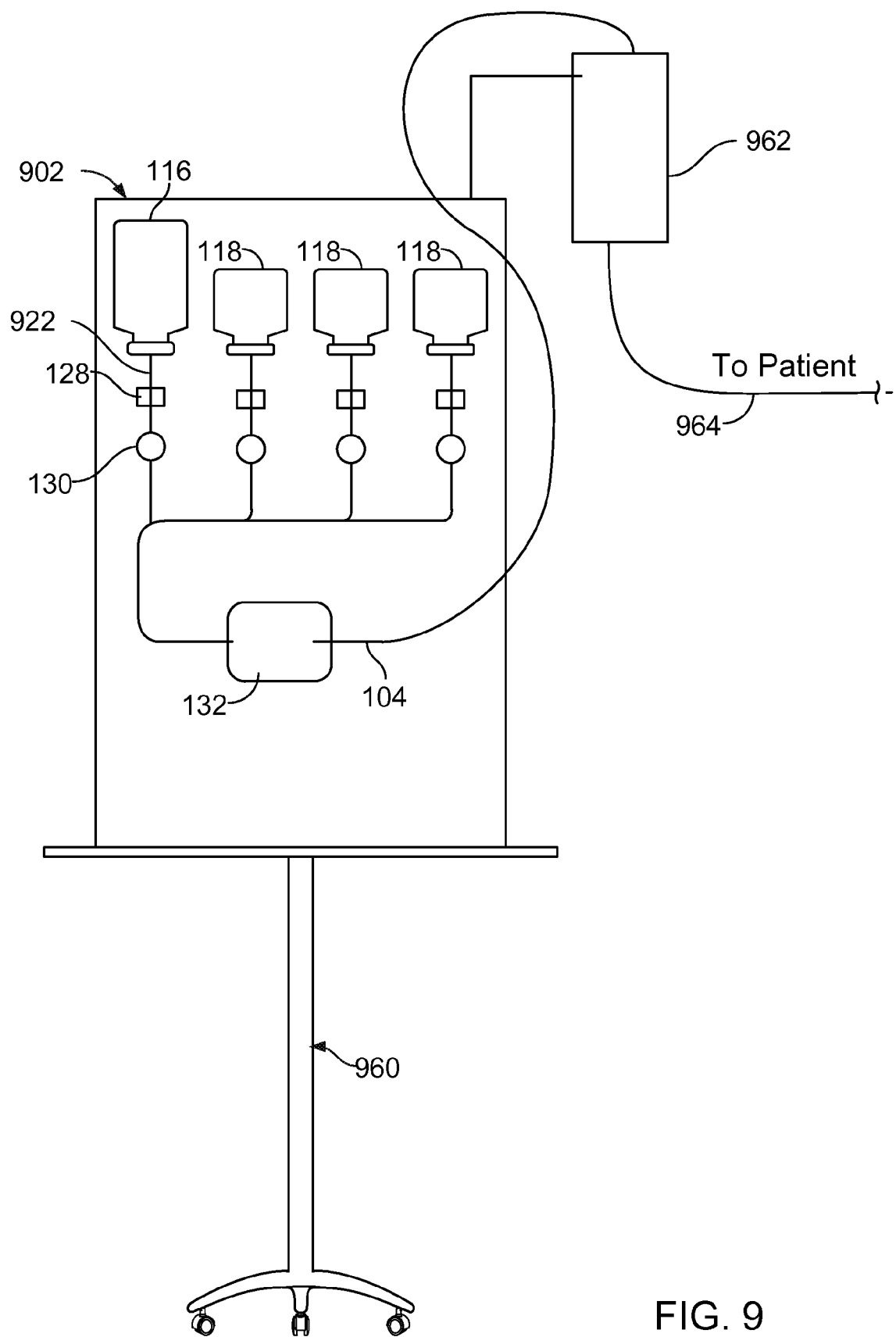
FIG. 9 is a schematic of a standalone drug delivery system.

While certain drug delivery devices described herein are provided as components of hemodialysis systems, the drug delivery devices can be used in any type of medical device that would benefit from drug infusion capabilities. Alternatively, the drug delivery devices described herein can be configured to be operated as stand alone machines (i.e., not connected to another medical device). FIG. 9 illustrates a stand alone drug delivery device 902, which is substantially the same as the drug delivery device 103 described above but sits on a wheeled cart 960. The drug delivery line 104 of this stand alone drug delivery device 902 is connected to a drip chamber. During use, the drug(s) is/are delivered from the vials 116, 118 to the drip chamber 962. The drug(s) is/are then delivered from the drip chamber 962 to the patient via a fluid line 964. The drip chamber 962, similar to the above-described drip chamber 106, helps to ensure that any air pulled into the system from the vials does not reach the patient. The drug delivery device 902 can be used in a manner similar to the drug delivery device 103 described above to deliver drugs to a patient and similar processes can be used to determine proper installation of medical fluid tubes 922.

While the drug vial holders 112, 114 are described as automatically spiking the vials 116, 118, manually spiking devices can alternative or additionally be used. For example, the Venofer® and Epogen® vial can be individually inserted into the drug vial holder 114 and manually applied to the spikes 120 of the cassette 107.

While the feeder lines 122 are described as being included in a cassette 107, the feeder lines 122 can also or additionally be separate lines, each line attached to a vial 116, 118. The feeder lines 122 can be manually positioned in the fluid detectors 128.

While the feeder lines 122 are described as being held in the housing of the fluid detector 128 by use of pressure, other methods may also be used to hold the feeder line 122 in position, for example, clips.

While the system is described as not signaling a lack of fluid in the feeder line 122 until fluid has been absent for three consecutive seconds, the duration of time that the system waits prior to signaling a lack of fluid may vary based on an expected state of the fluid in the feeder line 122. For example, when the feeder line is newly inserted into the fluid detector, the system may signal a lack of fluid each time a reading is beneath the threshold. During a period of time when medical fluid is being delivered to the patient, the system may not signal a lack of fluid in the feeder line 122 until fluid has been absent for three consecutive seconds. When the medical fluid delivery is nearing completion (e.g., the medical fluid has been pumped for predetermined period of time associated with complete delivery of the medical fluid from the vial), the system may signal a lack of fluid each time a reading is beneath the threshold.

While the fluid detector 816 is described as comparing the digital signal to threshold values, in some implementations, the threshold values may vary based on an expected state of the fluid in the feeder line 122. For example, when the feeder line is newly inserted into the fluid detector, the threshold may be increased, for example, by 100 mV, so that fluid is not detected if the digital signal is less than 2200 mV. When the feeder line is completely inserted and during a period of time when medical fluid is being delivered to the patient, the fluid detector 816 may compare the digital signal to a lower threshold value. For example, during delivery to the patient, fluid is not detected only if the digital signal is less than 2100 mV. When the medical fluid delivery is nearing completion, (e.g., the medical fluid has been pumped for predetermined period of time associated with complete delivery of the medical fluid from the vial), the fluid detector may compare the digital signal to a higher threshold value, for example, 2200 mV.

Figure 10:
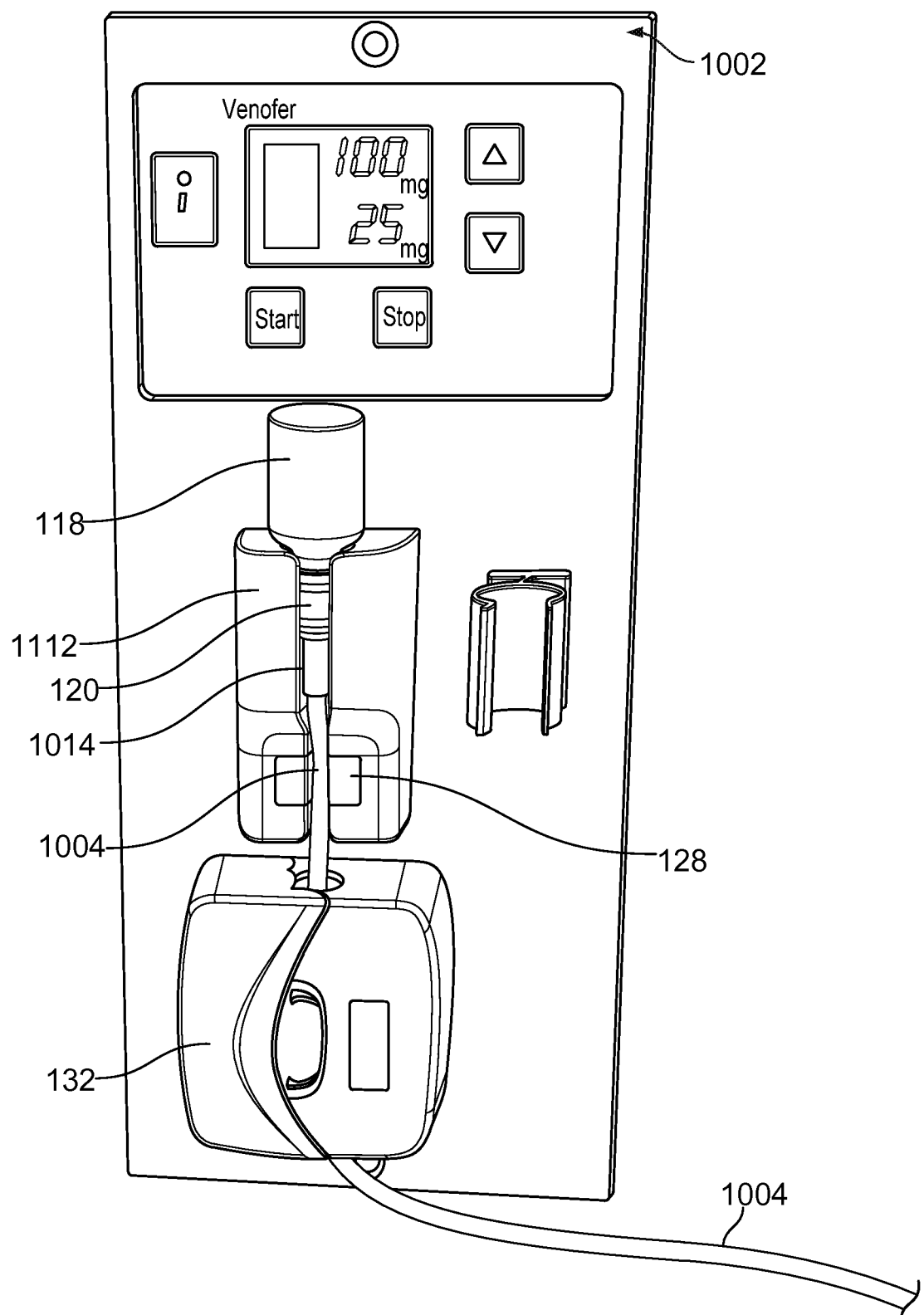
FIG. 10 is a perspective view of a modular drug delivery device that is configured for use with a single drug vial.

FIG. 10 illustrates a modular drug delivery device 1002 configured to retain only a single vial detached from the hemodialysis machine. The drug delivery device 1002 is substantially the same as the drug delivery device 103 described above. However, the drug delivery device 1002 illustrated in FIG. 10 includes a drug vial holder that includes only one channel 1014 instead of four. In addition, the drug administration fluid line set 107 that is used with the drug delivery device 1002 includes a single drug delivery line 1004 that is connected to the vial 118 via the drug vial spike 120. Similar process as described above can be used to determine proper installation of the single drug delivery line 1004, using fluid detector 128. The drug delivery device 1002 can be used where only one drug (e.g., Epogen®) is being administered to the patient and the prescribed dosage of that drug can be achieved with a single vial.

While drug delivery devices have been described above as including their own control unit, the drug delivery device can alternatively or additionally be configured to communicate with a control unit of the hemodialysis machine. In certain implementations, for example, the various components of the dialysis machine, including the drug delivery device components, are controlled by a single control unit of the hemodialysis machine.

While the pump has been described above to stop and occlude the feeder lines after priming the feeder lines, the drug delivery process can be configured to continue pumping after priming. For example, in certain implementations, the priming can be an initial part of a continuous drug delivery process.

While the process of detecting incorrect installation of the tubing by comparing signals from the fluid detector has been described above to start after priming the feeder lines, the process can start during the priming of the feeder lines. In certain implementations, for example, the first signal can be received during priming. The second signal can also be received during priming, or alternatively, after priming. The process can continue throughout the drug delivery process, so that second signals are received periodically through the duration of the drug delivery. In some implementations, the process can be stopped after a certain time.

While the methods of operating the drug delivery devices described above involve the user inputting a desired dosage prescription into the drug delivery device (e.g., typing the prescription into the touch screen of the drug delivery device), the prescription can alternatively be transmitted to the drug delivery device electronically. In certain implementations, for example, the desired prescription can be determined by a physician of the patient to be treated and the physician can input the prescription into a secured database or website. The prescription can then be automatically transmitted from the database to the control unit of the drug delivery device (e.g., to the control unit of the dialysis machine of which the drug delivery device is a part). This technique can help to prevent prescription input errors by the operator of the drug delivery device.

While drug vials have been described as being used in the drug delivery systems and methods described above, in certain implementations, other types of drug containers, such as bags, bottles, etc., are used.

While the drug delivery devices above have been described as being used to deliver Venofer® and/or Epogen®, it should be understood that the term "drug" as used herein incorporates pharmaceuticals as well as other fluids delivered to a patient intravenously. Other drugs that are contemplated to be automatically delivered to the patient in accordance with the various implementations of the invention, include but are not limited to, phosphate binders, vitamin D, and anticoagulants.

Implementations of the subject matter and the operations described in this specification can be implemented in digital electronic circuitry, or in computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus. Alternatively or in addition, the program instructions can be encoded on an artificially generated propagated signal, for example, a machine-generated electrical, optical, or electromagnetic signal, that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (for example, multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing The apparatus can include special purpose logic circuitry, for example, an FPGA (field programmable gate array) or an ASIC (application specific integrated circuit). The apparatus can also include, in addition to hardware, code that creates an execution environment for the computer program in question, for example, code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a standalone program or as a module, component, subroutine, object, or other unit suitable for use in a computing environment. A computer program may, but need not, correspond to a file in a file system. A program can be stored in a portion of a file that holds other programs or data (for example, one or more scripts stored in a markup language document), in a single file dedicated to the program in question, or in multiple coordinated files (for example, files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, for example, an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, for example, magnetic, magneto optical disks, or optical disks. However, a computer need not have such devices. Moreover, a computer can be embedded in another device, for example, a mobile telephone, a personal digital assistant (PDA), a mobile audio or video player, a game console, a Global Positioning System (GPS) receiver, or a portable storage device (for example, a universal serial bus (USB) flash drive), to name just a few. Devices suitable for storing computer program instructions and data include all forms of nonvolatile memory, media and memory devices, including by way of example semiconductor memory devices, for example, EPROM, EEPROM, and flash memory devices; magnetic disks, for example, internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a computer having a display device, for example, a CRT (cathode ray tube) or LCD (liquid crystal display) monitor, for displaying information to the user and a keyboard and a pointing device, for example, a mouse or a trackball, by which the user can provide input to the computer. Other kinds of devices can be used to provide for interaction with a user as well; for example, feedback provided to the user can be any form of sensory feedback, for example, visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's client device in response to requests received from the web browser.

While this specification contains many specific implementation details, these should not be construed as limitations on the scope of any disclosures or of what may be claimed, but rather as descriptions of features specific to particular implementations of particular disclosures. Certain features that are described in this specification in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

What is claimed is:

1. A dialysis system comprising:
    a dialysis machine;
    a control unit;
    a medical fluid tube connected to the dialysis machine;
    an ultrasonic transmitter positioned adjacent to the medical fluid tube;
    an ultrasonic receiver positioned adjacent to the medical fluid tube configured to receive one or more signals in response to the activation of the ultrasonic transmitter; and
    a computer storage medium encoded with computer program instructions that when executed by the dialysis system, causes the dialysis system to perform operations comprising:
        controlling repetitive activation of the ultrasonic transmitter, wherein controlling repetitive activation of the ultrasonic transmitter comprises, for each repetition:
            activating the ultrasonic transmitter for a first period of 2 to 15 milliseconds; and
            deactivating the ultrasonic transmitter for a second period of 998 to 985 milliseconds;

receiving a signal from the ultrasonic receiver during an activation of the ultrasonic transmitter; and determining that fluid is absent or present in a portion of the medical fluid tube based on a comparison between the signal and a threshold value.

2. The system of claim 1, wherein the computer storage medium is further encoded with computer program instructions that when executed by the dialysis system, causes the dialysis system to perform operations comprising:

storing an indicator of the absence or presence of fluid in a data structure, the data structure storing a plurality of indicators determined during previous activations of the ultrasonic transmitter.

3. The system of claim 2, wherein the computer storage medium is further encoded with computer program instructions that when executed by the dialysis system, causes the dialysis system to perform operations comprising:

raising an alarm upon determining that each indicator in the data structure indicates that fluid was absent from the portion of the medical fluid tube.

4. The system of claim 1, wherein the first period is 5 milliseconds and the second period is 995 milliseconds.

5. The system of claim 1, wherein the medical fluid tube has an outer diameter of less than 0.128 inch.

6. The system of claim 1, wherein the medical fluid tube has an inner diameter of less than 0.031 inch.

7. The system of claim 1, wherein the signal is a measure of voltage.

8. The system of claim 7, wherein the threshold value is a first value if fluid was determined to be present during the previous activation of the ultrasonic transmitter;

the threshold is a second value if the fluid was previously determined to be absent during the previous activation of the ultrasonic transmitter; and the first value is greater than the second value.

9. A computer-implemented method comprising:

on a control unit of a dialysis machine:

controlling, on a processor of the control unit, repetitive activation of an ultrasonic transmitter, wherein controlling repetitive activation of the ultrasonic transmitter comprises, for each repetition:

activating the ultrasonic transmitter for a first period of 2 to 15 milliseconds; and deactivating the ultrasonic transmitter for a second period of 998 to 985 milliseconds;

receiving, by the processor of the control unit, a signal from an ultrasonic receiver during an activation of the ultrasonic transmitter; and determining, by the processor of the control unit, that fluid is absent or present in a portion of a medical fluid tube of a drug delivery device based on a comparison between the signal and a threshold value.

10. The method of claim 9 further comprising:

storing an indicator of the absence or presence of fluid in a data structure, the data structure storing a plurality of indicators determined during previous activations of the ultrasonic transmitter.

11. The method of claim 10, further comprising:

raising an alert upon determining that each indicator in the data structure indicates that fluid was absent from the portion of the medical fluid tube.

12. The method of claim 9, wherein the first period is 5 milliseconds and the second period is 995 milliseconds.

13. The method of claim 9, wherein the medical fluid tube has an outer diameter of less than 0.128 inch.

14. The method of claim 9, wherein the medical fluid tube has an inner diameter of less than 0.031 inch.

15. The method of claim 9, wherein the signal is a measure of voltage.

16. The method of claim 15, wherein the threshold value is a first value if fluid was determined to be present during the previous activation of the ultrasonic transmitter;

the threshold is a second value if the fluid was previously determined to be absent during the previous activation of the ultrasonic transmitter; and the first value is greater than the second value.

17. A dialysis system comprising:

a dialysis machine;

a control unit;

an ultrasonic transmitter;

an ultrasonic receiver; and a computer storage medium encoded with computer program instructions that when executed by the dialysis system, causes the dialysis system to perform operations comprising:

controlling repetitive activation of the ultrasonic transmitter, wherein controlling repetitive activation of the ultrasonic transmitter comprises, for each repetition:

activating the ultrasonic transmitter for a first period of 2 to 15 milliseconds; and deactivating the ultrasonic transmitter for a second period of 998 to 985 milliseconds;

receiving a signal from the ultrasonic receiver during an activation of the ultrasonic transmitter; and determining that fluid is absent or present in a portion of a medical fluid tube based on a comparison between the signal and a threshold value.

18. The system of claim 17, wherein the computer storage medium is further encoded with computer program instructions that when executed by the dialysis system, causes the dialysis system to perform operations comprising:

storing an indicator of the absence or presence of fluid in a data structure, the data structure storing a plurality of indicators determined during previous activations of the ultrasonic transmitter.

19. The system of claim 18, wherein the computer storage medium is further encoded with computer program instructions that when executed by the dialysis system, causes the dialysis system to perform operations comprising:

raising an alarm upon determining that each indicator in the data structure indicates that fluid was absent from the portion of the medical fluid tube.

20. The system of claim 17, wherein the first period is 5 milliseconds and the second period is 995 milliseconds.

21. The system of claim 17, wherein the signal is a measure of voltage.

22. The system of claim 21, wherein the threshold value is a first value if fluid was determined to be present during the previous activation of the ultrasonic transmitter;

the threshold is a second value if the fluid was previously determined to be absent during the previous activation of the ultrasonic transmitter; and the first value is greater than the second value.

* * * * *